US012683023B2

(12) United States Patent
Pittman et al.

(10) Patent No.: US 12,683,023 B2
(45) Date of Patent: Jul. 14, 2026

(54) METHODS AND SYSTEMS FOR COMPREHENSIVE PATIENT SCREENING

(71) Applicant: United States Government as Represented by the Department of Veterans Affairs, Washington, DC (US)

(72) Inventors: James Pittman, Washington, DC (US); Elizabeth Floto, Washington, DC (US); Niloofar Afari, Washington, DC (US)

(73) Assignee: United States Government as Represented by the Department of Veterans Affairs, Washington, DC (US)

( * ) Notice: Subject to any disclaimer, the term of this patent is extended or adjusted under 35 U.S.C. 154(b) by 68 days.

(21) Appl. No.: 17/924,643

(22) PCT Filed: May 12, 2021

(86) PCT No.: PCT/US2021/031978
§ 371 (c)(1),
(2) Date: Nov. 10, 2022

(87) PCT Pub. No.: WO2021/231564
PCT Pub. Date: Nov. 18, 2021

(65) Prior Publication Data
US 2023/0187064 A1 Jun. 15, 2023

Related U.S. Application Data

(60) Provisional application No. 63/023,626, filed on May 12, 2020.

(51) Int. Cl.
G16H 40/67 (2018.01)
G16H 10/20 (2018.01)
(Continued)

(52) U.S. Cl.
CPC ............. *G16H 40/67* (2018.01); *G16H 10/20* (2018.01); *G16H 50/20* (2018.01); *G16H 50/30* (2018.01);
(Continued)

(58) Field of Classification Search
CPC ........ G16H 40/67; G16H 10/20; G16H 50/20; G16H 50/30; G16H 50/70; G16H 80/00; H04L 63/08
See application file for complete search history.

(56) References Cited

U.S. PATENT DOCUMENTS

2008/0015903 A1* 1/2008 Rodgers ................. G06Q 30/02
705/3
2011/0112852 A1 5/2011 Ware et al.
(Continued)

FOREIGN PATENT DOCUMENTS

WO WO-2018074996 A1 * 4/2018 ........... A61B 5/0022

OTHER PUBLICATIONS

V. W. Weedn et al., "Managing the community response to bioterrorist threats," in IEEE Engineering in Medicine and Biology Magazine, vol. 23, No. 1, pp. 162-170, Jan.-Feb. 2004, doi: 10.1109/MEMB.2004.1297188. (Year: 2004).*
(Continued)

*Primary Examiner* — Sun M Li
(74) *Attorney, Agent, or Firm* — Ballard Spahr LLP

(57) ABSTRACT

Comprehensive patient-facing screening may provide diagnostics, real-time alerts, and feedback relating to a wide range of health and medical-related issues. The methods and systems for comprehensive patient-facing screening described provide feasible, user-friendly use, and may improve operations, processes, and connection to clinical care for users, such as veterans.

19 Claims, 5 Drawing Sheets

(51) Int. Cl.

| | |
|---|---|
| *G16H 50/20* | (2018.01) |
| *G16H 50/30* | (2018.01) |
| *G16H 50/70* | (2018.01) |
| *G16H 80/00* | (2018.01) |
| *H04L 9/40* | (2022.01) |

(52) U.S. Cl.
CPC ............. *G16H 50/70* (2018.01); *G16H 80/00* (2018.01); *H04L 63/08* (2013.01)

(56) References Cited

U.S. PATENT DOCUMENTS

| | | | |
|---|---|---|---|
| 2014/0114680 A1 | 4/2014 | Mills et al. | |
| 2014/0247146 A1* | 9/2014 | Proud ..................... | H02J 50/10 |
| | | | 340/870.02 |
| 2015/0106020 A1* | 4/2015 | Chung ................... | G16H 40/67 |
| | | | 702/19 |
| 2015/0302538 A1* | 10/2015 | Mazar ................ | G08B 21/0211 |
| | | | 705/2 |
| 2017/0300648 A1* | 10/2017 | Charlap ................. | G16H 50/30 |
| 2019/0228848 A1* | 7/2019 | Saliman ................. | G16H 10/20 |
| 2020/0118458 A1* | 4/2020 | Shriberg ............... | G16H 40/67 |
| 2021/0027891 A1* | 1/2021 | Rajput ................... | G16H 70/40 |
| 2021/0183512 A1* | 6/2021 | Van Dusen ........ | G08B 21/0423 |
| 2023/0005574 A1* | 1/2023 | Sparks .................. | G16H 10/20 |

OTHER PUBLICATIONS

O. Rajabi Shishvan, D.-S. Zois and T. Soyata, "Machine Intelligence in Healthcare and Medical Cyber Physical Systems: A Survey," in IEEE Access, vol. 6, pp. 46419-46494, 2018, doi: 10.1109/ACCESS.2018.2866049. (Year: 2018).*

S. Scherer et al., "Automatic behavior descriptors for psychological disorder analysis," 2013 10th IEEE International Conference and Workshops on Automatic Face and Gesture Recognition (FG), Shanghai, China, 2013, pp. 1-8, doi: 10.1109/FG.2013.6553789. (Year: 2013).*

De Choudhury, Munmun, et al. "Predicting depression via social media." Proceedings of the international AAAI conference on web and social media. vol. 7. No. 1. 2013. (Year: 2013).*

M. Gandhi, V. K. Singh and V. Kumar, "IntelliDoctor—AI based Medical Assistant," 2019 Fifth International Conference on Science Technology Engineering and Mathematics (ICONSTEM), Chennai, India, 2019, pp. 162-168, doi: 10.1109/ICONSTEM.2019.8918778. (Year: 2019).*

K. H. Abdulkareem et al., "A Review of Fog Computing and Machine Learning: Concepts, Applications, Challenges, and Open Issues," in IEEE Access, vol. 7, pp. 153123-153140, 2019, doi: 10.1109/ACCESS.2019.2947542. (Year: 2019).*

Carol Habib, Abdallah Makhoul, Rony Darazi, Raphaël Couturier, Health risk assessment and decision-making for patient monitoring and decision-support using Wireless Body Sensor Networks, Information Fusion, vol. 47, 2019, pp. 10-22, (Year: 2019).*

Carol Habib, Abdallah Makhoul, Rony Darazi, Raphaël Couturier, Health risk assessment and decision-making for patient monitoring and decision-support using Wireless Body Sensor Networks, Information Fusion, vol. 47, 2019, pp. 10-22, (Year: 2019) (Year: 2019).*

O. Rajabi Shishvan, D.-S. Zois and T. Soyata, "Machine Intelligence in Healthcare and Medical Cyber Physical Systems: A Survey," in IEEE Access, vol. 6, pp. 46419-46494, 2018, doi: 10.1109/ACCESS.2018.2866049. (Year: 2018) (Year: 2018).*

* cited by examiner

200

PRESENT MEDICAL SCREENING QUESTIONS ⌐ 210

RECEIVE RESPONSES TO THE MEDICAL SCREENING QUESTIONS ⌐ 220

DETERMINE SCORES FOR THE  MEDICAL SCREENING QUESTIONS ⌐ 230

STORE THE SCORES ⌐ 240

DETERMINE AN ALERT CONDITION ⌐ 250

300

310

PRESENT MEDICAL SCREENING QUESTIONS

320

RECEIVE RESPONSES TO THE MEDICAL SCREENING QUESTIONS

330

DETERMINE SCORES FOR THE MEDICAL SCREENING QUESTIONS

340

DETERMINE LIKELIHOOD OF A MEDICAL ISSUE

350

STORE AN INDICATOR OF THE LIKELIHOOD OF THE MEDICAL ISSUE

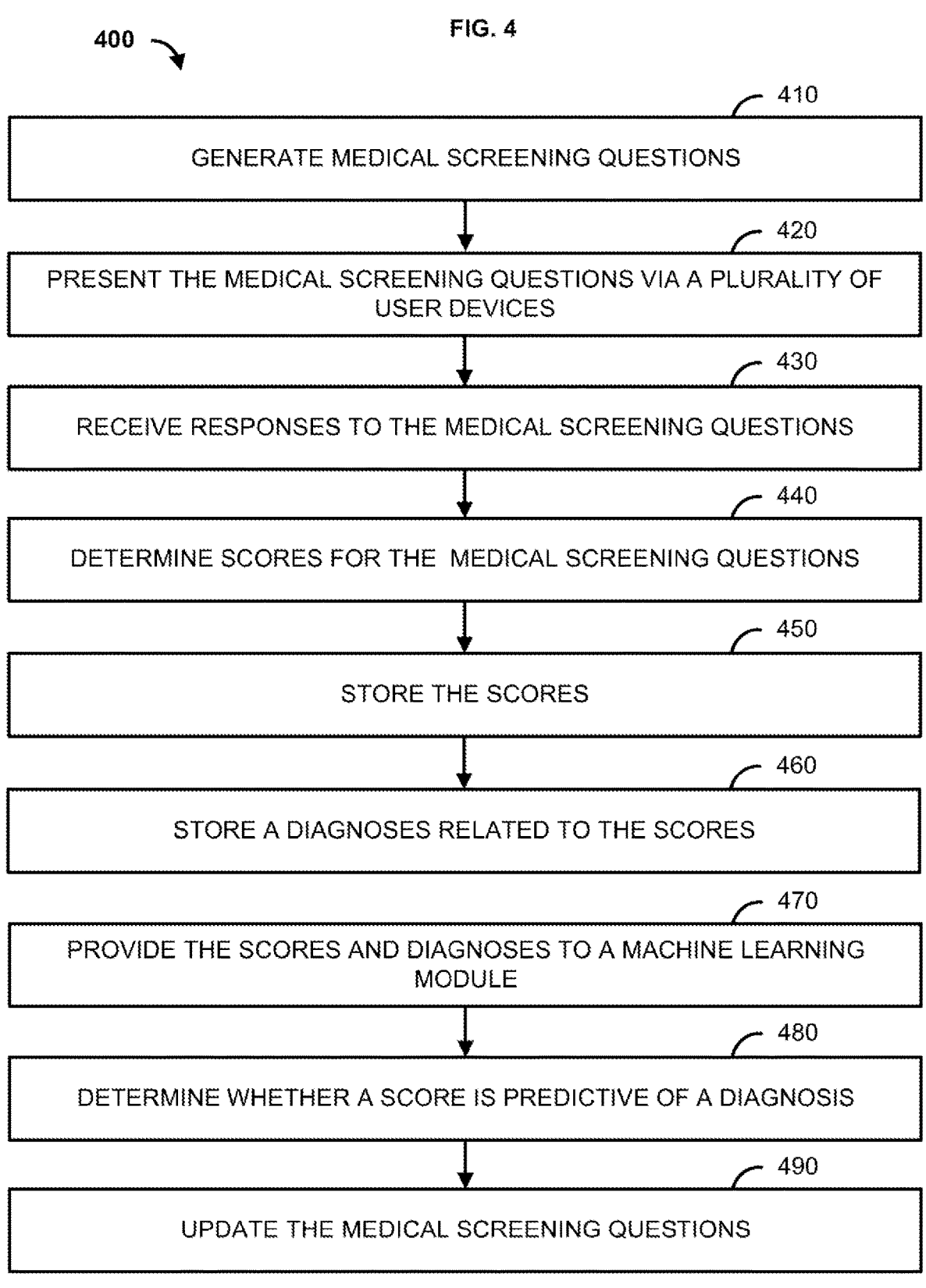

410
GENERATE MEDICAL SCREENING QUESTIONS

420
PRESENT THE MEDICAL SCREENING QUESTIONS VIA A PLURALITY OF USER DEVICES

430
RECEIVE RESPONSES TO THE MEDICAL SCREENING QUESTIONS

440
DETERMINE SCORES FOR THE MEDICAL SCREENING QUESTIONS

450
STORE THE SCORES

460
STORE A DIAGNOSES RELATED TO THE SCORES

470
PROVIDE THE SCORES AND DIAGNOSES TO A MACHINE LEARNING MODULE

480
DETERMINE WHETHER A SCORE IS PREDICTIVE OF A DIAGNOSIS

490
UPDATE THE MEDICAL SCREENING QUESTIONS

METHODS AND SYSTEMS FOR COMPREHENSIVE PATIENT SCREENING

CROSS REFERENCE TO RELATED APPLICATIONS

This application is a national phase filing under 35 U.S.C. § 371 of International Application No. PCT/US2021/031978, filed May 12, 2021, which claims priority to and the benefit of U.S. Provisional Application No. 63/023,626, filed May 12, 2020, the entireties of which are hereby incorporated by reference therein.

BACKGROUND

Globally, individual mental health is a concern. Particularly in countries like the United States, there is an increased concern for the mental status of individuals that may have been exposed to traumatic incidents and/or environments, such as veterans. Institutions, such as the Veterans Health Administration, responsible for providing quality care to healthcare participants (e.g., enrollees, patients, etc.), routinely work to identify and treat potential mental health and other disorders (e.g., depression, posttraumatic stress disorder (PTSD), etc.). However, many healthcare participants (e.g., enrollees, patients, etc.), despite receiving healthcare services, may have a diagnosable mental illness and/or other disorder that goes undetected. Systematic screening can improve the detection of mental health and/or other disorders. Patients are often interviewed with standardized screening questions and responses are manually and/or verbally entered into a computerized patient record system. Manual and/or verbal entrance of patient records into patient record systems is laborious, subject to transcription and/or a translation error, and/or subject to incomplete/incorrect information due to patient self-reporting anxiety.

SUMMARY

It is to be understood that both the following general description and the following detailed description are exemplary and explanatory only and are not restrictive. Methods and systems for comprehensive patient screening are described. A user device (e.g., a mobile device, a smart device, computing device, etc.) may periodically collect and/or integrate patient data/information with a patient data/information system in communication with one or more health and medical analysis devices. The user device may generate and/or display, via an interface, medical screening questions, such as medial screening questions and/or measures associated with a patient's sociodemographic and service history, military sexual trauma (MST), traumatic brain injury (TBI), somatic symptoms (e.g., pain in various areas, dizziness, cardiovascular issues/concerns, gastrointestinal issues/concerns, and fatigue/sleep issues/concerns, etc.), pain intensity, tobacco and alcohol use, posttraumatic stress disorder (PTSD) symptoms, depression symptoms, anxiety symptoms, insomnia, and/or the like. The user device may determine, for each response (e.g., a tactile response, audio response, a patient-provided response, etc.) to the medical screening questions and/or measures, a score (e.g., a score on a scale from 1-10, etc.). Each score generated and/or determined based on responses to the medical screening questions may be associated with user information (e.g., a user profile, an electronic medical record (EMR) associated with the patient, a user account, etc.). Scores associated with the user information, based on the scores satisfying a threshold, may be used to determine an alert condition and/or generate an alert/notification. An alert condition may be an indication that a user (e.g., patient, subject, etc.) is at risk for an emergency medical condition. For example, a score determined from a response to a medical screening question associated with pain intensity may exceed a threshold value of 4 (on a scale from 1-10) may cause based on one or more associated thresholds, may cause an alert condition to be determined and/or an alert/notification to be generated/sent (e.g., sent to a medical and/or healthcare device/professional, etc.).

This summary is not intended to identify critical or essential features of the disclosure, but merely to summarize certain features and variations thereof. Other details and features will be described in the sections that follow.

BRIEF DESCRIPTION OF THE DRAWINGS

The accompanying drawings, which are incorporated in and constitute a part of this specification, together with the description, serve to explain the principles of the methods and systems:

FIG. 4 shows a flowchart of an example method for comprehensive patient screening.

DETAILED DESCRIPTION

Figure 1:
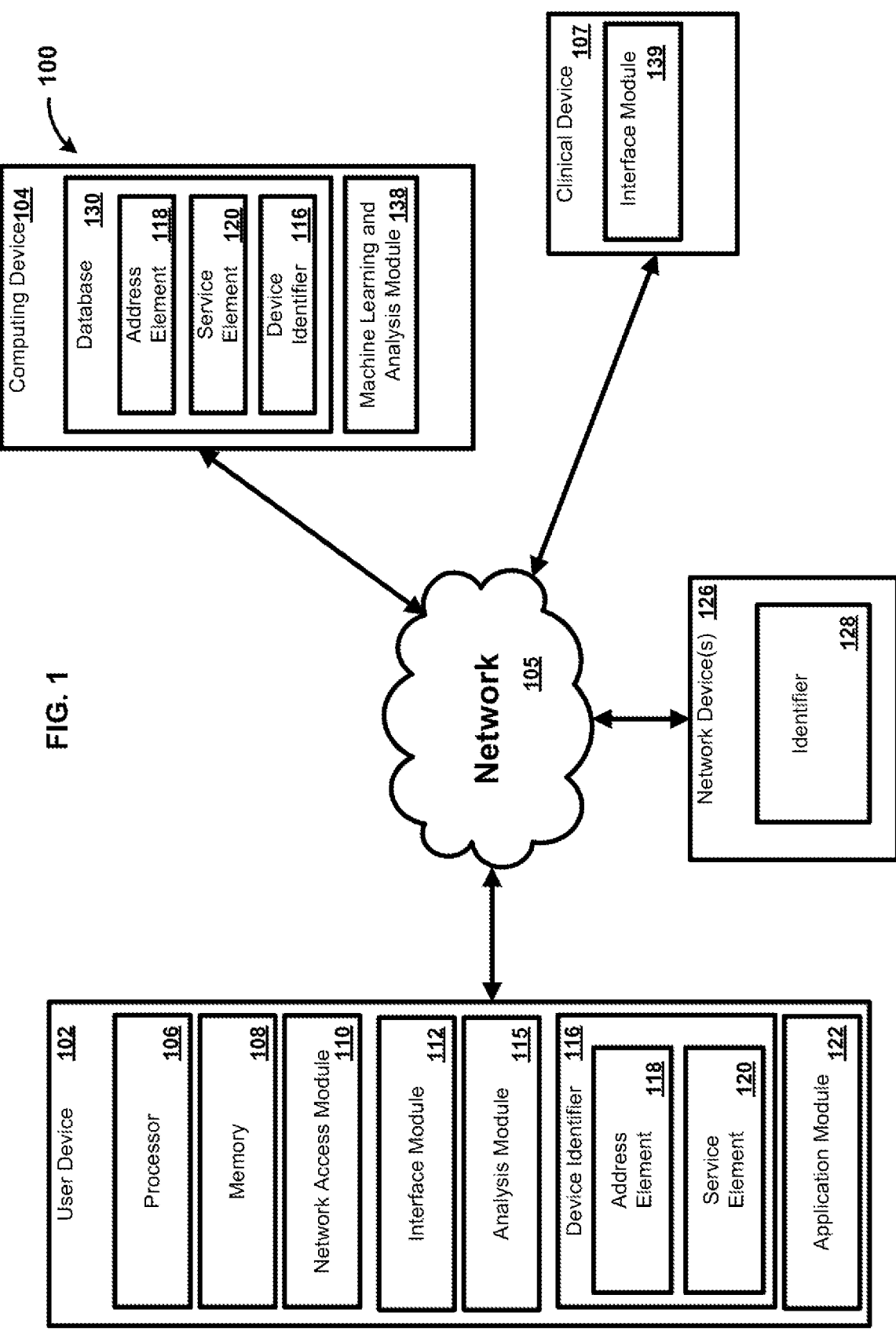
FIG. 1 shows an example system for comprehensive patient screening.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another configuration includes from the one particular value and/or to the other particular value. When values are expressed as approximations, by use of the antecedent "about," it will be understood that the particular value forms another configuration. It will be further understood that the endpoints of each of the ranges are significant both in relation to the other endpoint, and independently of the other endpoint.

"Optional" or "optionally" means that the subsequently described event or circumstance may or may not occur, and that the description includes cases where said event or circumstance occurs and cases where it does not.

Throughout the description and claims of this specification, the word "comprise" and variations of the word, such as "comprising" and "comprises," means "including but not limited to," and is not intended to exclude other components, integers or steps. "Exemplary" means "an example of" and is not intended to convey an indication of a preferred or ideal configuration. "Such as" is not used in a restrictive sense, but for explanatory purposes.

It is understood that when combinations, subsets, interactions, groups, etc. of components are described that, while specific reference of each various individual and collective combinations and permutations of these may not be explicitly described, each is specifically contemplated and described herein. This applies to all parts of this application including, but not limited to, steps in described methods.

Thus, if there are a variety of additional steps that may be performed it is understood that each of these additional steps may be performed with any specific configuration or combination of configurations of the described methods.

As will be appreciated by one skilled in the art, hardware, software, or a combination of software and hardware may be implemented. Furthermore, a computer program product on a computer-readable storage medium (e.g., non-transitory) having processor-executable instructions (e.g., computer software) embodied in the storage medium. Any suitable computer-readable storage medium may be utilized including hard disks, CD-ROMs, optical storage devices, magnetic storage devices, memresistors, Non-Volatile Random Access Memory (NVRAM), flash memory, or a combination thereof.

Throughout this application reference is made to block diagrams and flowcharts. It will be understood that each block of the block diagrams and flowcharts, and combinations of blocks in the block diagrams and flowcharts, respectively, may be implemented by processor-executable instructions. These processor-executable instructions may be loaded onto a general-purpose computer, special purpose computer, or other programmable data processing apparatus to produce a machine, such that the processor-executable instructions which execute on the computer or other programmable data processing apparatus create a device for implementing the functions specified in the flowchart block or blocks.

These processor-executable instructions may also be stored in a computer-readable memory that may direct a computer or other programmable data processing apparatus to function in a particular manner, such that the processor-executable instructions stored in the computer-readable memory produce an article of manufacture including processor-executable instructions for implementing the function specified in the flowchart block or blocks. The processor-executable instructions may also be loaded onto a computer or other programmable data processing apparatus to cause a series of operational steps to be performed on the computer or other programmable apparatus to produce a computer-implemented process such that the processor-executable instructions that execute on the computer or other programmable apparatus provide steps for implementing the functions specified in the flowchart block or blocks.

Accordingly, blocks of the block diagrams and flowcharts support combinations of devices for performing the specified functions, combinations of steps for performing the specified functions and program instruction means for performing the specified functions. It will also be understood that each block of the block diagrams and flowcharts, and combinations of blocks in the block diagrams and flowcharts, may be implemented by special purpose hardware-based computer systems that perform the specified functions or steps, or combinations of special purpose hardware and computer instructions.

This detailed description may refer to a given entity performing some action. It should be understood that this language may in some cases mean that a system (e.g., a computer) owned and/or controlled by the given entity is actually performing the action.

A user device (e.g., a mobile device, a smart device, computing device, etc.) may periodically collect and/or integrate patient data/information with a patient data/information system in communication with one or more health and medical analysis devices. The user device may generate and/or display, via an interface, medical screening questions, such as medial screening questions and/or measures associated with a patient's sociodemographic and service history, military sexual trauma (MST), traumatic brain injury (TBI), somatic symptoms (e.g., pain in various areas, dizziness, cardiovascular issues/concerns, gastrointestinal issues/concerns, and fatigue/sleep issues/concerns, etc.), pain intensity, tobacco and alcohol use, posttraumatic stress disorder (PTSD) symptoms, depression symptoms, anxiety symptoms, insomnia, and/or the like.

For each response (e.g., tactile response, audio response, patient-provided response, etc.) to the medical screening questions and/or measures, a score (e.g., a score on a scale from 1-10, etc.) may be determined. In some instances, the user device may determine scores to the medical screening questions, such as by accessing data/information associated with the medical screening questions and/or measures and correlating each response to the medical screening questions and/or measures to the data/information associated with the medical screening questions and/or measures. In some instances, the user device communicates with a computing device (e.g., cloud-based device, server, electronic medical records management device, etc.) and provide the responses to the medical screening questions to the computing device. The computing device may determine scores for the medical screening questions. Scores to the medical screening questions may be determined, for example, by accessing data/information associated with the medical screening questions (and/or measures) and correlating each response to the medical screening questions (and/or measures) to the data/information associated with the medical screening questions (and/or measures). For example, a neural network and/or machine learning may be used to correlate each response to the medical screening questions (and/or measures) to data/information associated with the medical screening questions (and/or measures).

Data/information associated with the medical screening questions (and/or measures) may be and/or associated with a scale. For example, data/information associated with pain intensity may be associated with a scale from 1-10, where scores/values of 4 or greater are considered to be clinically significant pain, and/or the like. The data/information associated with the medical screening questions and/or measures may be and/or associated with any scale and/or score. Each response to the medical screening questions and/or measures may be associated with a score that is determined relative to a scale and/or the like associated with each medical screening question.

Each score generated and/or determined based on responses to the medical screening questions may be associated with user information (e.g., a user profile, an electronic medical record (EMR) associated with the patient, a user account, etc.). Each score generated and/or determined based on responses to the medical screening questions may be used to determine a likelihood that a user will be diagnosed with a medical issue. In some instances, the user device and/or computing device (e.g., via the neural network and/or machine learning, etc.) may determine the likelihood that a user will be diagnosed with a medical issue based on a score generated and/or determined from responses to the medical screening questions. Scores satisfying a threshold (e.g., a clinical threshold, etc.) may indicate a medical issue. For example, scores may be used to determine an alert condition. An alert condition may be an indication that a user (e.g., patient, subject, etc.) is at risk for an emergency medical condition. An alert/notification (e.g., a clinical notification and/or reminder, etc.) may be determined and/or generated based on an alert condition. For example, a score determined from a response to a medical screening question associated with pain intensity may exceed a threshold value of 4 (on a scale from 1-10), and may alert condition to be determined and/or an alert/notification to be generated/sent (e.g., sent to a medical and/or healthcare device/professional, etc.).

The methods and systems for comprehensive patient screening described herein may lower the cost of medical care and reduce the analytical burdens on clinicians faced with increasing amounts of clinical data. The methods and systems for comprehensive patient screening described may save time, improved data capture, and improve early detection of mental issues and/or disorders. The methods and systems for comprehensive patient screening described may aid triage and referral of patients to healthcare and/or medical professionals, lower the cost of medical care, and reduce the analytical burdens associated with systematic screening (e.g., manual and/or verbal entrance of patient records into patient record systems, etc.).

FIG. 1 shows a system 100 for comprehensive patient screening. One skilled in the art will appreciate that provided herein is a functional description and that the respective functions may be performed by software, hardware, or a combination of software and hardware. The system 100 may include a network 105. The network 105 may be a private and/or public network, such as the Internet, a local area network, a wide area network, a cellular network, a satellite network, combinations thereof, and/or the like. The network 105 may include and/or support any form of wired and/or wireless communication.

The system 100 may include one or more network devices 126. The one or more network device(s) 126 may facilitate the connection of a device, such as a user device 102, to the network 105. The one or more network device(s) 126 may be part of a cellular network. The one or more network device(s) 126 may be and/or include a wireless access point (WAP). The network device(s) 126 may allow one or more wireless devices to connect to a wired and/or wireless network using Wi-Fi, Bluetooth, or any desired method or standard. The network device(s) 126 may be and/or include a dual-band wireless access point. The network device(s) 126 may be configured with a first service set identifier (SSID) (e.g., associated with a user network or private network) to function as a local network for a particular user or users. The network device(s) 126 may be configured with a second service set identifier (SSID) (e.g., associated with a public/community network or a hidden network) to function as a secondary network or redundant network for connected communication devices.

The network device(s) 126 may include an identifier 128. One or more identifiers (e.g., the identifier 128, etc.) may be or relate to an Internet Protocol (IP) Address IPV4/IPV6 or a media access control address (MAC address) or the like. The identifier 128 may be a unique identifier for facilitating communications on a physical network. The network device(s) 126 may include a distinct identifier 128 that is associated with a physical location of the network device(s) 126.

The system 100 may include a user device 102 (e.g., a mobile device, a smart device, a computing device, etc.) in communication with a computing device 104 (e.g., cloud-based device, server, electronic medical records management device, etc.) and/or a clinical device 107. In some instances, the system 100 may include multiple user devices (e.g., user device 102) in communication with the computing device 104 and/or multiple clinical devices (e.g., clinical device). The user device 102 may be in communication with the computing device 104 and/or a clinical device 107 via a long-range communication technique (e.g., Internet, cellular, satellite, and the like), via a short-range communication technique (e.g., BLUETOOTH®, ZigBee, Z-wave, near-field communication, infrared, etc.), and/or via any communication technique.

The computing device 104 and/or a clinical device 107 may be disposed locally or remotely relative to the user device 102. The user device 102 and the computing device 104 can be in communication via the network 105. In some instances, the system 100 may include multiple user devices (e.g., the user device 102, etc.), computing devices (e.g., the computing device 104, etc.), and/or clinical devices (e.g., the clinical device 107, etc.) in communication via the network 105.

The user device 102 may be associated with a user identifier or device identifier 116. The device identifier 116 may be and/or include a mobile directory number (MDN), a mobile identification number (MIN), an international mobile subscriber identity (IMSI), an international mobile equipment identifier (IMEI), and/or the like. The device identifier 116 may be and/or include any identifier, token, character, string, and/or the like, for differentiating one user or user device (e.g., user device 102) from another user or user device. The device identifier 116 may identify a user or user device as belonging to a particular class of users or user devices. The device identifier 116 may comprise information relating to the user device 102 such as a manufacturer, a model or type of device, a service provider associated with the user device 102, a state of the user device 102, a locator, and/or a label or classifier. The device identifier 116 may comprise and/or be associated with information relating to one or more applications installed on and/or associated with the user device 102. Other and/or any information may be represented by the device identifier 116.

The device identifier 116 may comprise an address element 118 and a service element 120. The address element 118 may include or provide a mobile directory number (MDN), an internet protocol address, a network address, a media access control (MAC) address, an Internet address, and/or the like. The address element 118 may be relied upon to establish a communication session between the user device 102, the computing device 104, the clinical device 107, and/or any other device/network/system. The address element 118 may be used as an identifier or locator of the user device 102. The address element 110 may be persistent for a particular network.

The service element 120 may comprise an identification of a service provider associated with the user device 102 and/or with the class of user device 102. The class of the user device 102 may be related to a type of device, a capability of a device, a type of service being provided, and/or a level of service (e.g., business class, service tier, service package, etc.). The service element 120 may comprise information relating to and/or provided by a communication service provider (e.g., an application service provider, an Internet service provider) that is providing or enabling data/information flow such as application (e.g., a software application, etc.) and/or communication services to the user device 102. The service element 120 may comprise information relating to a preferred service provider for one or more particular services relating to the user device 102. The address element 118 may be used to identify or retrieve data/information from the service element 120, or vice versa. The address element 118 and the service element 120 may be stored remotely from the user device 102 and retrieved by one or more devices such as the user device 102 and/or the computing device 104. Other information may be represented by the service element 112.

The user device 102 can comprise a processor 106. The processor 106 may be and/or include any suitable microprocessor or microcontroller, such as a low-power application-specific controller (ASIC) and/or a field-programmable gate array (FPGA) designed or programmed specifically for the task of controlling the user device 102 as described herein, or a general-purpose central processing unit (CPU) (e.g., a CPU based on 80×86 architecture as designed by Intel™ or AMD™, or a system-on-a-chip as designed by ARM™. The processor 106 can be coupled to auxiliary devices or modules of the user device 102 via a bus or other coupling.

The user device 102 may include a non-transitory memory module 108 coupled to the processor 106. The memory 108 can comprise a random access memory (RAM) for storing program instructions and data/information for execution and/or processing by the processor 106 during control of the user device 102. The memory module 108 may store user (e.g., patient, subject, etc.) data/information, and/or medical screening information (e.g., one or more measures relating to patient health and/or mental status). Medical screening information may be any data/information used to elicit information and/or responses associated with user health (e.g., mental health), status, and/or wellbeing. For example, medical screening information may include, but is not limited to, questions and/or measures associated with a user (e.g., patient, subject, etc.) sociodemographic and service history, military sexual trauma (MST), traumatic brain injury (TBI), somatic symptoms (e.g., pain in various areas, dizziness, cardiovascular issues/concerns, gastrointestinal issues/concerns, and fatigue/sleep issues/concerns, etc.), pain intensity, tobacco and alcohol use, posttraumatic stress disorder (PTSD) symptoms, depression symptoms, anxiety symptoms, insomnia, and/or the like. When the user device 102 is powered off and/or in an inactive state, medical screening information, program instructions, and/or any other data/information may be stored in long-term memory, such as a non-volatile magnetic optical, an electronic memory storage device (not shown), and/or the like. The RAM and/or the long-term memory may store and/or include one or more application programming interfaces (APIs) associated with one or more applications associated with and/or installed on the user device 102, such as an application associated with comprehensive patient screening. The RAM and/or the long-term memory may include a non-transitory computer-readable medium storing program instructions that, when executed by the processor 106, cause the user device 102 to perform all or part of one or more methods and/or operations described herein. Program instructions and/or the like may be written in any suitable high-level language, such as C, C++, C#, Java™, and/or the like. Program instructions and/or the like may be compiled to produce machine-language code for execution by the processor 106.

The user device 102 can include a network access module 110. The network access module 110 may enable the user device 102 to be coupled to and/or in communication with one or more ancillary devices such as via a network device 126 (e.g., an access point, etc.) associated with a wireless telephone network, local area network, service provider, the Internet, and/or the like. The user device 102 (processor 106) may share data/information (e.g., comprehensive patient screening data/information, etc.) with the one or more ancillary devices via the network access module 110. The shared data/information can comprise application data/information, call data/information, messaging data/information, usage data/information, location data/information, operational data/information associated with the user device 102, a status of the user device 102, a status and/or operating condition of one or more the components of the user device 102, text to be used in a message, and/or any other data. The user device 102 may be configured to receive control instructions from one or more ancillary devices via the network access module 110. A configuration of the user device 102, an operation of the user device 102, and/or any other settings of the user device 102, may be controlled by the one or more ancillary devices, such as another user device 102 and/or the computing device 104, via the network access module 110.

The user device 102 may include an interface module 112. The interface module 112 may include and/or be associated with a communication interface such as a web browser (e.g., Internet Explorer, Mozilla Firefox, Google Chrome, Safari, or the like). Other software, hardware, and/or interfaces can be used to provide communication between the user and one or more of the user device 102, the computing device 104, the clinical device 107, and/or any other device. The interface module 112 can request or query various files from a local source and/or a remote source, such as data/information associated with and/or including medical screening questions and/or measures. The medical screening questions and/or measures may be associated with user sociodemographic and service history, military sexual trauma (MST), traumatic brain injury (TBI), somatic symptoms (e.g., pain in various areas, dizziness, cardiovascular issues/concerns, gastrointestinal issues/concerns, and fatigue/sleep issues/concerns, etc.), pain intensity, tobacco and alcohol use, posttraumatic stress disorder (PTSD) symptoms, depression symptoms, anxiety symptoms, insomnia, and/or the like.

The interface module 112 may provide an interface to a user to interact with the user device 102, the computing device 104, the clinical device 107, and/or any other device. The interface module 112 can include any interface for presenting information to a user, such as one or more visual interfaces (e.g., displays, monitors, etc.), audio interfaces (e.g., microphones, speakers, etc.), and/or any other input/output component. The interface module 112 can include any interface for receiving information from a user, such as one or more tactile interfaces (e.g., keyboards, touch pads, etc.), audio interfaces (e.g., microphones, speakers, etc.), and/or any other input/output component. The interface module 112 can be and/or include any interface for presenting information to the user, such as medical screening questions and/or related measures associated with user sociodemographic and service history, military sexual trauma (MST), traumatic brain injury (TBI), somatic symptoms (e.g., pain in various areas, dizziness, cardiovascular issues/concerns, gastrointestinal issues/concerns, and fatigue/sleep issues/concerns, etc.), pain intensity, tobacco and alcohol use, posttraumatic stress disorder (PTSD) symptoms, depression symptoms, anxiety symptoms, insomnia, and/or the like. The interface module 112 can be and/or include any interface for receiving information to the user, such as responses to medical screening questions (and/or measures). The interface module 112 may be any interface for presenting and/or receiving any information to/from the user.

The user device 102 may include an analysis module 115. The analysis module 115 may determine data/information associated with medical screening questions and/or measures (e.g., responses to medical screening questions), such as a score that may indicate a medical issue. For example, the analysis module 115 may determine, for each response (e.g., tactile response, audio response, patient-provided response, etc.) to medical screening questions and/or measures, a score (e.g., a score on a scale from 1-10, etc.). The analysis module 115 may access data/information associated with the medical screening questions and/or measures (e.g., stored in the memory 108 or any other location, etc.) and correlate each response to the medical screening questions and/or measures to the data/information associated with the medical screening questions and/or measures.

The analysis module 115 may determine scores for the medical screening questions. The analysis module 115 may, for example, determine scores to the medical screening questions by accessing data/information associated with the medical screening questions (and/or measures) and correlating each response to the medical screening questions (and/or measures) to the data/information associated with the medical screening questions (and/or measures). In some instances, the analysis module 115 may determine scores to the medical screening questions by accessing data/information associated with the medical screening questions (and/or measures) and using machine learning to correlate each response to the medical screening questions (and/or measures) to the data/information associated with the medical screening questions (and/or measures). The analysis module 115 may associate each medical screening question and/or associated measure with a scale (e.g., a nominal scale, an ordinal scale, an interval scale, a ratio scale, etc.) of a plurality of scales. Each scale of the plurality of scales may a quantitative and/or a standard system for grading a measure. The analysis module 115 may determine scores by determining, for each measure, a scale. The analysis module 115 may, for each response to the plurality of medical screening questions, based on an associated scale of the plurality of scales, may scale the response according to a medical screening question and/or measure. Each scaled response to a medical screening question may represent a score. The analysis module 115 may total (e.g., sum, average, means-square, etc.) scores derived from responses to determine an overall score associated with a user. The overall score may be associated with the health and/or wellbeing of the user. The overall score may indicate possible health and/or wellbeing issues. The user device 102 may display (via the interface module 112) a score and/or an overall score associated with a user. The user device 102 may determine scores based on any method.

The user device 102 may be in communication with the computing device 104. The computing device 104 may communicate with the user device 102 for providing data and/or services. The computing device 104 may allow the user device 102 to interact with remote resources such as data, devices, and files. The computing device may be configured as (or disposed at) a central location (e.g., a headend, or processing facility), which may receive content (e.g., data, input programming) from multiple sources. The computing device 104 may combine the content from the multiple sources and may distribute the content to user (e.g., subscriber) locations via a distribution system.

The computing device 104 may manage the communication between the user device 102 (and/or multiple user devices 102) and a database 130 for sending and receiving data therebetween. The database 130 may store a plurality of files (e.g., web pages), user identifiers or records, or other information. The user device 102 may request and/or retrieve a file from the database 130. The database 130 may store information relating to the user device 102 such as the address element 110 and/or the service element 112. The computing device 104 may obtain the device identifier 116 from the user device 102 and retrieve information from the database 130 such as the address element 118 and/or the service elements 112. The computing device 104 may obtain the address element 110 from the user device 102 and may retrieve the service element 112 from the database 130, or vice versa. Any information may be stored in and retrieved from the database 130. The database 130 may be disposed remotely from the computing device 104 and accessed via a direct or indirect connection. The database 130 may be integrated with the computing system 104 or some other device or system. The database 130 may be and/or be associated with an electronic medical records (EMR) system. The database 130 may include an EMR associated with a user and/or multiple users. Each EMR may include data/information such as a treatment and medical history associated with a user. The EMR may include the user's health (e.g., mental health, etc.) history and records cataloged in a standardized format. The EMR may be and/or include secure and/or encrypted data/information that may be searched, accessed, and/or queried to provide real-time information associated with medical decision-making. Scores derived from medical screening questions may be associated with an EMR associated with a user.

In some instances, the computing device 104 (e.g., a cloud-based device, a server, an electronic medical records management device, etc.) may determine scores derived from responses to medical screening questions. For example, the user device 102 (via the interface module 112) may receive responses to medical screening questions and send the responses to the computing device 104. The user device 102 may send the responses to the computing device 104 via a long-range communication technique (e.g., Internet, cellular, satellite, and the like), via a short-range communication technique (e.g., BLUETOOTH®, ZigBee, Z-wave, near-field communication, infrared, etc.), and/or via any communication technique. The computing device 104 may receive the responses to the medical screening questions and determine scores based on the responses received.

The computing device 104 may access data/information associated with the plurality of measures (e.g., stored in the database 130, etc.) to determine the one or more scores. The computing device 104 may correlate each response to the medical screening questions (and/or measures) to the data/information associated with the medical screening questions (and/or measures). The computing device 104 may associate each medical screening question and/or associated measure with a scale (e.g., a nominal scale, an ordinal scale, an interval scale, a ratio scale, etc.) of a plurality of scales. Each scale of the plurality of scales may a quantitative and/or a standard system for grading a measure. The computing device 104 may determine scores by determining, for each measure, a scale. The computing device 104 may, for each response to the plurality of medical screening questions, based on an associated scale of the plurality of scales, may scale the response according to a medical screening question and/or measure. Each scaled response to a medical screening question may represent a score. The computing device 104 may total (e.g., sum, average, means-square, etc.) scores derived from responses to determine an overall score associated with a user. The overall score may be associated with the health and/or wellbeing of the user. The overall score may indicate possible health and/or wellbeing issues. The computing device may determine scores by any method and may provide the scores to the user device.

The computing device 104 may provide the scores to the user device 102 via a long-range communication technique (e.g., Internet, cellular, satellite, and the like), via a short-range communication technique (e.g., BLUETOOTH®, ZigBee, Z-wave, near-field communication, infrared, etc.), and/or via any communication technique. The user device 102 may present, display, and/or cause display of the one or more scores. The user device 102 may present, display, and/or cause display of the one or more scores. The user device 102 may present, display, and/or cause display of data/information associated with the one or more scores, such as graphical, statistical, and/or any other analytical data/information associated with the one or more scores. For example, the user device 102 may present, display, and/or cause display of a graph that depicts user scores (and or responses to medical screening questions) over a time period and/or range.

The computing device 104 may store (e.g., via the database 130, etc.) scores. Storing scores may include associating the scores with user information (e.g., a user profile, an electronic medical record (EMR) associated with the patient, a user account, etc.) associated with the user. Storing the scores may include storing a score for each medical screening question and/or measure. Storing the scores may include storing additional data/information associated with the user, screening question, and/or the like.

One or more scores may be compiled with additional medical information associated with a measure. Specific diagnoses, and prescribed services and/or treatments may be determined based on a score. In some instances, the user device 102 may determine specific diagnoses, and prescribed services and/or treatments. For example, an application associated with the user device may determine specific diagnoses, and prescribed services and/or treatments based on responses to medical screening questions. In some instances, the computing device 104 may determine specific diagnoses, and prescribed services and/or treatments based on responses to medical screening questions received from the user device 102.

An alert condition may be determined based on a score derived from a medical screening question. An alert condition may be and/or include an indication that a user is at risk for an emergency medical condition associated with a measure related to the medical screening question. Scores may be compiled with additional medical information associated with each measure of a plurality of measures, and specific diagnosis, and prescribed services and/or treatments may be determined based on an alert condition. Scores may be accessed and/or analyzed according to one or more rules associated with medical screening questions and/or associated measures. For example, a rule associated with a measure for pain intensity may dictate that user scores that satisfy a threshold value may indicate an alert condition. Such that a score/value of 4 or greater (on an associated scale ranging from values 1-10) are considered to be clinically significant pain, and therefore indicative of an alert condition. An alert condition may be determined based on any rule associated with the associated medical screening question and/or associated measure. In some instances, the user device 102 (via the analysis module 115, etc.) may determine the alert condition. For example, an application associated with the user device 102 may determine the alert condition. In some instances, the computing device 104 may determine the alert condition based on the responses received from the user device 102.

The computing device 104 may include a machine learning and analysis module 138. In some instances, a machine learning and analysis module 138 may determine an alert condition and/or the likelihood that the user will be diagnosed with a medical issue related to a measure of the plurality of measures, based on a score for the measure. The machine learning and analysis module 138 may be and/or include a neural network.

In some cases, the machine learning and analysis module 138 may perform, in whole or in part, the analytical function of the system 100. The machine learning and analysis module 138 may be configured to approximate the knowledge of a clinician/physician and a standard of mental, physical, and medical care by making discriminating judgments based on a probable cause of mental, physical, and/or medical-based diagnoses determined through the analysis of user-health data (e.g., responses to medical screening questions, etc.) in view of a set or sets (e.g., a dataset and/or datasets, etc.) of clinical methodologies. The machine learning and analysis module 138 may use both fuzzy logic, Boolean models, and/or the like. Fuzzy logic, in contrast to more deterministic Boolean models, may provide an analytical output of clinical/medical data sets in terms of clinical/medical probabilities rather than more rigid absolutes.

The machine learning and analysis module 138 may access and/or determine clinical probabilities, such as probable medical and/or health alert conditions. The machine learning and analysis module 138 may include contemporaneous determined and stored user health data (e.g., from medical screening questions, etc.). The machine learning and analysis module 138 may comprise a collection of clinical data/information, such as historical symptoms, diagnoses, and outcomes, along with time development of medical issues and measures associated with a sociodemographic and service history, military sexual trauma (MST), traumatic brain injury (TBI), somatic symptoms (e.g., pain in various areas, dizziness, cardiovascular issues/concerns, gastrointestinal issues/concerns, and fatigue/sleep issues/concerns, etc.), pain intensity, tobacco and alcohol use, posttraumatic stress disorder (PTSD) symptoms, depression symptoms, anxiety symptoms, insomnia, and/or the like. The clinical data/information may be coded and/or encoded and input into the machine learning and analysis module 138 to populate and/or train the computing device 104 with clinical data/information that may be used to determine, derived, and/or predict clinical, medical, health, and diagnostic outcomes, such as one or more alerts conditions.

Scores derived from responses to the medical screening questions may be used to create a dataset. The machine learning and analysis module 138 may compare the dataset to previously stored datasets and/or information. Comparing the dataset to stored datasets and/or information may indicate a possible diagnosis of a medical issue associated with a measure of the plurality of measures. In some instances, scores derived from responses to the medical screening questions from multiple users and/or multiple user devices 102 may be used to create a training dataset. The training dataset may be used to train the machine learning and analysis module 138. When new data/information (e.g., clinical information, responses to medical screening questions, training datasets, etc.) is provided to the machine learning and analysis module 138, the machine learning and analysis module 138 may update any stored data/information and adapt to any changing parameters (e.g., changes to a dataset, etc.) associated with the clinical data/information. The machine learning and analysis module 138 may verify conclusions, diagnoses, and/or the like for accuracy and/or significance. The machine learning and analysis module 138 may store test cases, appropriate outcomes, and the relative occurrence of misidentification of the proper outcome and/or diagnosis. The machine learning and analysis module 138 may establish a threshold of acceptable misidentifications or misdiagnoses.

When an alert condition (and/or any other condition associated with the plurality of medical screening questions) is determined, such as based on a score for a measure of the plurality of measures, the clinical device 107 and/or an associated clinician may be determined. The computing device 104 may use information associated with the user device 102, such as the device identifier 116 and/or an identifier associated with the user to determine the clinical device 107 and/or an associated clinician. The computing device 104 may use the device identifier 116 and/or an identifier associated with the user to determine the user information (e.g., user profile, electronic medical record (EMR) associated with the patient, user account, whitelist, etc.).

The user information may indicate one or more clinical devices 107 and/or clinicians associated with the user and/or user device 102. A clinical devices 107 and/or clinician be associated with various medical screening question and/or measures, such as measures and/or information associated with a user's sociodemographic and service history, military sexual trauma (MST), traumatic brain injury (TBI), somatic symptoms (e.g., pain in various areas, dizziness, cardiovascular issues/concerns, gastrointestinal issues/concerns, and fatigue/sleep issues/concerns, etc.), pain intensity, tobacco and alcohol use, posttraumatic stress disorder (PTSD) symptoms, depression symptoms, anxiety symptoms, insomnia, and/or the like. In some instances, the clinical devices 107 and/or clinician may be determined based on a measure, such as based on a score derived from medical questions for a particular measure. The clinical devices 107 and/or clinician may be associated with a respective measure of the plurality of measures based on a clinical ability of a clinician associated with a clinical device 107 to respond to, treat, diagnose, provide care for, and/or otherwise address any issue relating to and/or associated with the measure. The clinical devices 107 and/or clinician may each be ranked based on a clinical ability of a clinician associated with a clinical device 107 to respond to, treat, diagnose, provide care for, and/or otherwise address any issue relating to and/or associated with a measure. The computing device 104 may use the rank associated with the clinical device 107 and/or an associated clinician to determine the clinical device 107 and/or an associated clinician.

The computing device 104 (or user device 102) may send a notification (e.g., a signal, a message, an email, a text, etc.) to the clinical device 107 based on determining an alert condition, medical diagnosis, predictive diagnosis, and/or any other related information associated with a user of the user device 102. The computing device 104 (or user device 102) may send the notification to the clinical device 107 via a long-range communication technique (e.g., Internet, cellular, satellite, and the like), via a short-range communication technique (e.g., BLUETOOTH®, ZigBee, Z-wave, near-field communication, infrared, etc.), and/or via any communication technique. The notification may be sent to the clinical device 107 via an application. For example, the notification may be sent to the clinical device 107 via an application program interface (API) associated with the user device 102, the computing device 104, the clinical device 107, and/or the like.

The clinical device 107 may include an interface module 139. The interface module 139 may include and/or be associated with a communication interface such as a web browser (e.g., Internet Explorer, Mozilla Firefox, Google Chrome, Safari, or the like). Other software, hardware, and/or interfaces can be used to provide communication between the clinician and one or more of the clinical device 107, the computing device 104, the user device 102, and/or any other device. The interface module 139 can request or query various files from a local source and/or a remote source, such as data/information associated with and/or including medical screening questions and/or measures. The interface module 139 may provide an interface for a clinician to interact with the clinical device 107, the computing device 104, the user device 102, and/or any other device. The interface module 139 can include any interface for presenting information to a clinician, such as one or more visual interfaces (e.g., displays, monitors, etc.), audio interfaces (e.g., microphones, speakers, etc.), and/or any other input/output component. The interface module 139 can include any interface for receiving information from a clinician/user, such as one or more tactile interfaces (e.g., keyboards, touch pads, etc.), audio interfaces (e.g., microphones, speakers, etc.), and/or any other input/output component. The interface module 139 can be and/or include any interface for presenting information to the clinician/user, such as scores from medical screening questions, predictive diagnoses of medical and/or health issues, and/or any data/information.

The interface module 139 may enable a clinician/user to view information about a notification and/or alarm condition, such as information about a user/patient status, physiological parameter values, trend data, audio/video of the user/patient, combinations of the same, or the like. The notification may cause the clinical device 107 to perform an action. For example, the notification may cause the clinical device to schedule an appointment (e.g., via an appointment scheduling system, online/web-based system, etc.) to meet with the clinician and/or a clinical staff associated with the clinical device 107. The interface module 139 may provide functionality for a clinician/user to respond to a notification, annotate an alarm/diagnosis, indicate that the clinician can or cannot respond to the notification, schedule an appointment for medical, mental, and/or health care/treatment, and/or the like.

Figure 2:
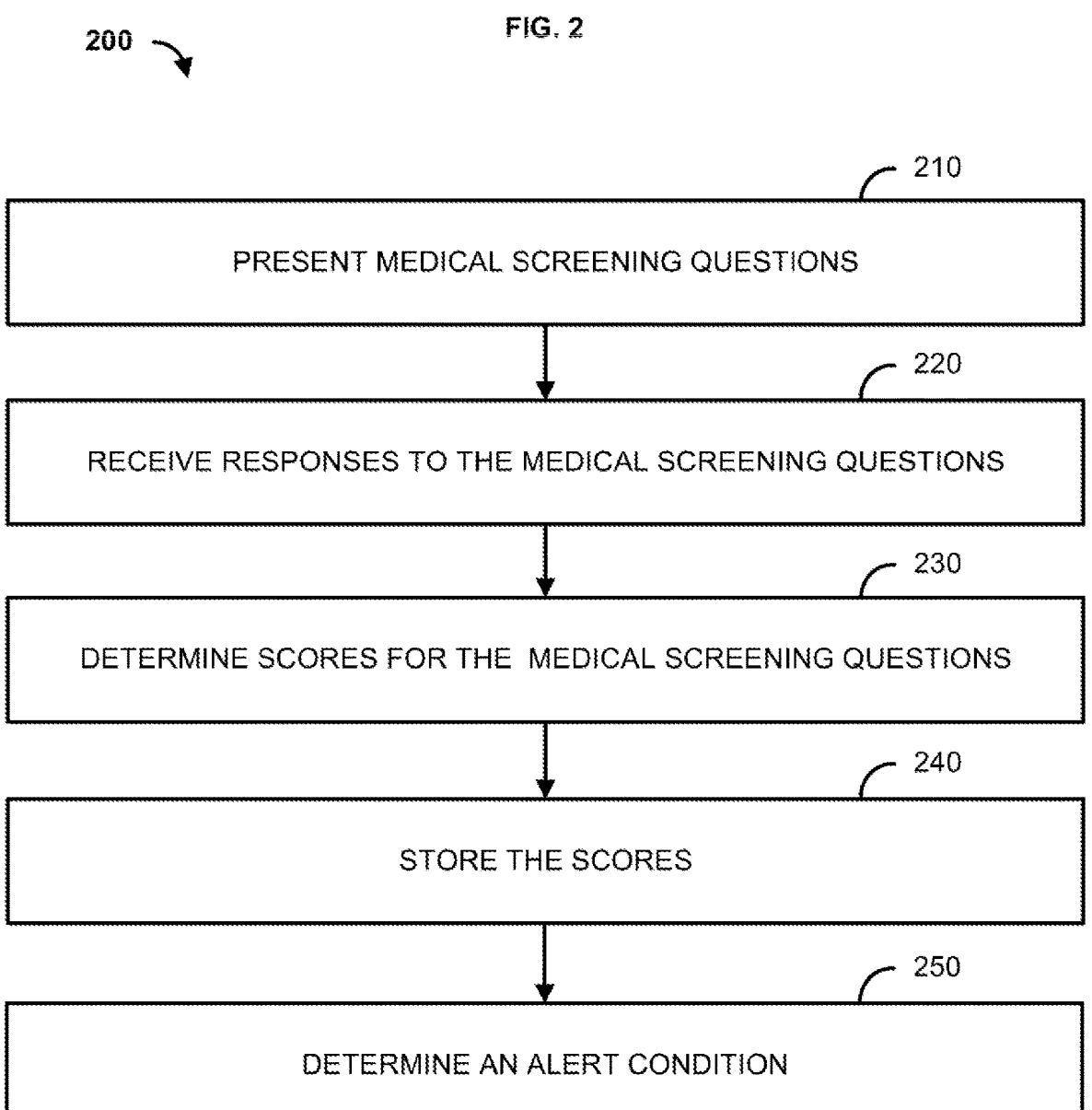
FIG. 2 shows a flowchart of an example method for comprehensive patient screening.

FIG. 2 shows a flowchart of an example method 200 for comprehensive patient screening. To aid in the provision of health care to users (e.g., veterans, medical screening patients, health care participants, etc.), at 210, a user device (e.g., a mobile device, a smart device, computing device, etc.) may present, display, and/or cause display of a plurality of medical screening questions. For example, the user device may include and/or be associated with a display for presenting/displaying a plurality of medical screening questions. In some instances, the user device may be configured with an application that causes a plurality of medical screening questions to be presented and/or displayed. The plurality of medical screening questions may include questions associated with a plurality of measures associated with health and wellbeing.

The plurality of measures may include measures and/or information associated with a user's sociodemographic and service history, military sexual trauma (MST), traumatic brain injury (TBI), somatic symptoms (e.g., pain in various areas, dizziness, cardiovascular issues/concerns, gastrointestinal issues/concerns, and fatigue/sleep issues/concerns, etc.), pain intensity, tobacco and alcohol use, posttraumatic stress disorder (PTSD) symptoms, depression symptoms, anxiety symptoms, insomnia, and/or the like. The plurality of measures may include measures and/or information associated with any health and/or wellbeing issue.

Questions and/or measures for sociodemographic and service history may include and/or be used to determine a user's age, gender, race, ethnicity, education level, relationship status, primary sources of income, and/or the like. For example, a user such as a military/war veteran, via the user device, may be presented questions that elicit responses and/or information associated with pay grade, a branch of service, number of deployments, and exposure to combat. Questions and/or measures for sociodemographic and service history may be associated with any question and/or query that elicits a response from the user. Questions and/or measures for sociodemographic and service history may be any questions and/or measures for sociodemographic and service history.

Questions and/or measures for military sexual trauma (MST) may include and/or be associated with sexual activity while in active duty. For example, a measure for MST may be associated with a question such as "when you were in the military, did you ever receive uninvited and unwanted sexual attention (e.g., unwanted touching, cornering, pressure for sexual favors, verbal remarks, etc.)?" and "when you were in the military, did anyone ever use force or the threat of force to have sex with you against your will?" Questions and/or measures for MST may be associated with any question and/or query that elicits a response from the user. Questions and/or measures for MST may be any questions and/or measures for MST.

Questions and/or measures for traumatic brain injury (TBI) may include and/or be associated with events occurring during a user's military tenure in which an injury could have occurred, immediate symptoms following the event, as well as current, new, and/or worsening symptoms. Questions and/or measures for TBI may be associated with any question and/or query that elicits a response from the user. Questions and/or measures for TBI may be any questions and/or measures for TBI.

Questions and/or measures for somatic symptoms may be used to assess and/or determine a user's somatic symptoms. For example, user's may be queried regarding the extent that the user is bothered by pain in various areas, dizziness, cardiovascular problems, gastrointestinal issues, and fatigue or sleep problems. Questions and/or measures for somatic symptoms may be associated with any question and/or query that elicits a response from the user. Questions and/or measures for somatic symptoms may be any questions and/or measures for somatic symptoms and/or the like.

Questions and/or measures for pain intensity, posttraumatic stress disorder (PTSD), depression symptoms, anxiety symptoms, and insomnia may include and/or be associated with any question and/or query that elicits a response from the user. Questions and/or measures for pain intensity, PTSD, depression symptoms, anxiety symptoms, and insomnia may be any questions and/or measures for and/or associated with pain intensity, posttraumatic stress disorder (PTSD), depression symptoms, anxiety symptoms, insomnia, and/or the like.

The user device may present, display, and/or cause display of any question, inquiry, and/or the like associated with user health and wellbeing. The user device may present, display, and/or cause display of any question, inquiry, and/or the like.

At 220, responses to the plurality of medical screening questions may be received. The user device may receive responses to the medical screening questions. The responses to the medical screening questions may include tactile responses, audio responses, and/or any other response associated with a user. For example, the user device may present, display, and/or cause display of a question relating to MST such as "when you were in the military, did you ever receive uninvited and unwanted sexual attention (e.g., unwanted touching, cornering, pressure for sexual favors, verbal remarks, etc.)?" The user may provide a response, such as "yes," or "no" to the question by providing an audible response, clicking on and/or accessing a displayed field, typing a response via an input/output component of the user device (e.g., keyboard, touch screen, etc.), and/or any other means of providing a response.

At 230, one or more scores may be determined. A score (e.g., a dichotomous score, a polytomous score, etc.) may be determined for each measure of the plurality of measures, based on the response to each of the plurality of medical screening questions. Each measure of the plurality of measures may be associated with a scale (e.g., a nominal scale, an ordinal scale, an interval scale, a ratio scale, etc.) of a plurality of scales. Each scale of the plurality of scales may a quantitative and/or a standard system for grading a measure of the plurality of measures. The one or more scores may be determined by determining, for each measure of the plurality of measures, a scale of the plurality of scales. Each response to the plurality of medical screening questions, based on an associated scale of the plurality of scales, may be scaled. Each scaled response to the plurality of medical screening questions may represent a score of the one or more scores. In some instances, each score of the one or more scores may be totaled (e.g., summed, averaged, means-squared, etc.) to determine an overall score associated with the user. The overall score may be associated with the health and/or wellbeing of the user. The overall score may indicate possible health and/or wellbeing issues.

In some instances, the user device may determine the one or more scores. For instance, an application associated with and/or installed on the user device may determine the one or more scores based on the responses to the plurality of medical screening questions. The user device may determine the one or more scores based on any method. In some instances, a computing device (e.g., cloud-based device, server, electronic medical records management device, etc.) may determine the one or more scores. For example, the user device may receive the responses to the plurality of medical screening questions and send the responses to the computing device. The user device may send the responses to the computing device via a long-range communication technique (e.g., Internet, cellular, satellite, and the like), via a short-range communication technique (e.g., BLU-ETOOTH®, ZigBee, Z-wave, near-field communication, infrared, etc.), and/or via any communication technique. The computing device may receive the responses to the plurality of medical screening questions and determine the one or more scores. The computing device may access data/information associated with the plurality of measures to determine the one or more scores. The computing device may determine the one or more scores by any method and may provide the one or more scores to the user device. The computing device may provide the one or more scores to the user device via a long-range communication technique (e.g., Internet, cellular, satellite, and the like), via a short-range communication technique (e.g., BLUETOOTH®, ZigBee, Z-wave, near-field communication, infrared, etc.), and/or via any communication technique.

At 240, the one or more scores may be stored. Storing the one or more scores may include associating the one or more scores with user information (e.g., a user profile, an electronic medical record (EMR) associated with the patient, a user account, etc.) associated with the user. Storing the one or more scores may include storing at least the score for each measure of the plurality of measures. Storing the one or more scores may include storing additional data/information associated with the user.

In some instances, the user device may store the one or more scores. For example, an application associated with the user device may access and/or be in communication with a data/information repository (e.g., an electronic medical record, etc.) associated with the user device. In some instances, the computing device may store the one or more scores. The computing device may include and/or be associated with an electronic medical record (EMR). For example, the user device may establish a communication session with the computing device. The user device may send the computing device a device identifier associated with the user device and an identifier associated with the user, such as a patient identifier and/or the like. The computing device may use the device identifier to authenticate the user device. For example, the computing device may associate the device identifier with stored user information (e.g., a user profile, an electronic medical record (EMR) associated with the patient, a user account, a whitelist, etc.). The user information may indicate one or more devices (e.g., user devices) that are authenticated and/or authorized to access an EMR system. The computing device may use the identifier associated with the user (e.g., patient identifier, etc.) to authenticate the user. For example, the computing device may associate the identifier associated with the user (e.g., patient identifier, etc.) with stored user information (e.g., a user profile, an electronic medical record (EMR) associated with the patient, a user account, a whitelist, etc.). The user information may indicate one or more users (e.g., patients, subjects, etc.) that are authenticated and/or authorized to access and/or be associated with the EMR system. The computing device may determine, based on the identifier associated with the user (e.g., patient identifier, etc.), information associated with the user, such as an electronic medical record (EMR) and/or the like.

An EMR associated with a user may include data/information such as a treatment and medical history associated with the user. The EMR may include the user's health (e.g., mental health, etc.) history and records cataloged in a standardized format. The EMR may be and/or include secure and/or encrypted data/information that may be searched, accessed, and/or queried to provide real-time information associated with medical decision-making. The one or more scores may be associated with the EMR associated with the user.

At 250, an alert condition may be determined. An alert condition may be determined based on a score for a measure of the plurality of measures. An alert condition may be and/or include an indication that the user is at risk for an emergency medical condition associated with a measure of the plurality of measures. The one or more scores may be compiled with additional medical information associated with each measure of the plurality of measures, and specific diagnosis, and prescribed services and/or treatments may be determined based on an alert condition. In some instances, the user device may determine the alert condition. For example, an application associated with the user device may determine the alert condition. In some instances, the computing device (and/or a device/system in communication with the computing device, etc.) may determine the alert condition based on the responses received from the user device.

To determine an alert condition, each score of the one or more scores may be accessed and/or analyzed according to one or more rules associated with each measure of the plurality of measures. For example, a rule associated with a measure for pain intensity may dictate that user scores that satisfy a threshold value may indicate an alert condition. Such that a score/value of 4 or greater (on an associated scale ranging from values 1-10) are considered to be clinically significant pain, and therefore indicative of an alert condition. An alert condition may be determined based on any rule associated with each measure of the plurality of measures.

In some instances, an alert condition may be determined by a neural network (e.g., a machine learning device/module/system, etc.). For example, to determine a likelihood that a user will have a diagnosis of a medical issue associated with a measure of the plurality of measures, based on a score for the measure. The computing device and/or the user device may be in communication with (and/or comprise) a neural network (e.g., a machine learning device/module/system, etc.). The neural network may include contemporaneous determined and stored user health data (e.g., from medical screening questions, etc.). The neural network may comprise a collection of clinical data/information, such as historical symptoms, diagnoses, and outcomes, along with time development of medical issues and measures associated with a sociodemographic and service history, military sexual trauma (MST), traumatic brain injury (TBI), somatic symptoms (e.g., pain in various areas, dizziness, cardiovascular issues/concerns, gastrointestinal issues/concerns, and fatigue/sleep issues/concerns, etc.), pain intensity, tobacco and alcohol use, posttraumatic stress disorder (PTSD) symptoms, depression symptoms, anxiety symptoms, insomnia, and/or the like. The clinical data/information may be coded and/or encoded and input into the neural network to populate and/or train the network with clinical data/information that may be used to determine, derived, and/or predict clinical, medical, health, and diagnostic outcomes, such as one or more alerts conditions. When new data/information (e.g., clinical information, responses to medical screening questions, etc.) is provided to the neural network, the network may update any stored data/information and adapt to any changing parameters associated with the clinical data/information. The neural network (and/or use of the neural network) may verify conclusions, diagnoses, and/or the like for accuracy and/or significance. The neural network may store test cases, appropriate outcomes, and the relative occurrence of misidentification of the proper outcome and/or diagnosis. The neural network may establish a threshold of acceptable misidentifications or misdiagnoses.

When an alert condition (and/or any other condition associated with the plurality of medical screening questions) is determined, such as based on a score for a measure of the plurality of measures, a clinical device (e.g., the clinical device 107, a server, etc.) and/or an associated clinician may be determined. In some cases, the user device, based on determining the alert condition, may determine the clinical device and/or an associated clinician. For example, an application associated with and/or installed on the user device, based on determining the alert condition, may determine the clinical device and/or an associated clinician. In some cases, the computing device, based on determining the alert condition, may determine the clinical device and/or an associated clinician.

In some instances, the device identifier associated with the user device and/or the identifier associated with the user may be used to determine the clinical device and/or an associated clinician. For example, the device identifier associated with the user device and/or the identifier associated with the user may be used to determine the user information (e.g., user profile, electronic medical record (EMR) associated with the patient, user account, whitelist, etc.). The user information may indicate one or more clinical devices and/or clinicians associated with the user and/or user device. The one or more clinical devices and/or clinicians may each be associated with a measure (or one or more measures) of the plurality of measures. In some instances, the one or more clinical devices and/or clinicians may be determined based on a measure of the plurality of measures, such as based on a score derived from the plurality of medical questions for a particular measure of the plurality of measures. For example, each measure of the plurality of measures may be associated with one or more clinical devices and/or clinicians. The one or more one or more clinical devices and/or clinicians may be associated with a respective measure of the plurality of measures based on a clinical ability of a clinician associated with a clinical device to respond to, treat, diagnose, provide care for, and/or otherwise address any issue relating to and/or associated with the measure. The one or more clinical devices and/or clinicians may each be ranked based on a clinical ability of a clinician associated with a clinical device to respond to, treat, diagnose, provide care for, and/or otherwise address any issue relating to and/or associated with the measure. The rank associated with the clinical device and/or an associated clinician may be used to determine the clinical device and/or an associated clinician.

The clinical device (e.g., the clinical device 107, a server, etc.) and/or an associated clinician may receive a notification (e.g., a signal, a message, an email, a text, etc.). In some cases, the user device, based on determining the alert condition, may send the notification to the clinical device. For example, an application associated with and/or installed on the user device, based on determining the alert condition, may send the notification to the clinical device. In some cases, the computing device, based on determining the alert condition, may send the notification to the clinical device. The notification may be sent to the clinical device via a long-range communication technique (e.g., Internet, cellular, satellite, and the like), via a short-range communication technique (e.g., BLUETOOTH®, ZigBee, Z-wave, near-field communication, infrared, etc.), and/or via any communication technique. The notification may be sent to the clinical device via an application associated with and/or installed on the user device, associated with the computing device, and/or the like. For example, the notification may be sent to the clinical device via an application program interface (API) associated with the user device, the computing device, the clinical device, and/or the like.

The notification may cause the clinical device to perform an action. For example, the notification may cause the clinical device to schedule an appointment (e.g., via an appointment scheduling system, online/web-based system, etc.) to meet with the clinician and/or a clinical staff associated with the clinical device. The notification may cause the clinical device to send data/information associated with the user of the user device to the user device and/or computing device. The data/information associated with the user of the user device may include appointment reminders, health and/or medical advice/instructions, information relating to a measure of the plurality of measures, and/or the like. The data/information associated with the user may include any data/information.

Figure 3:
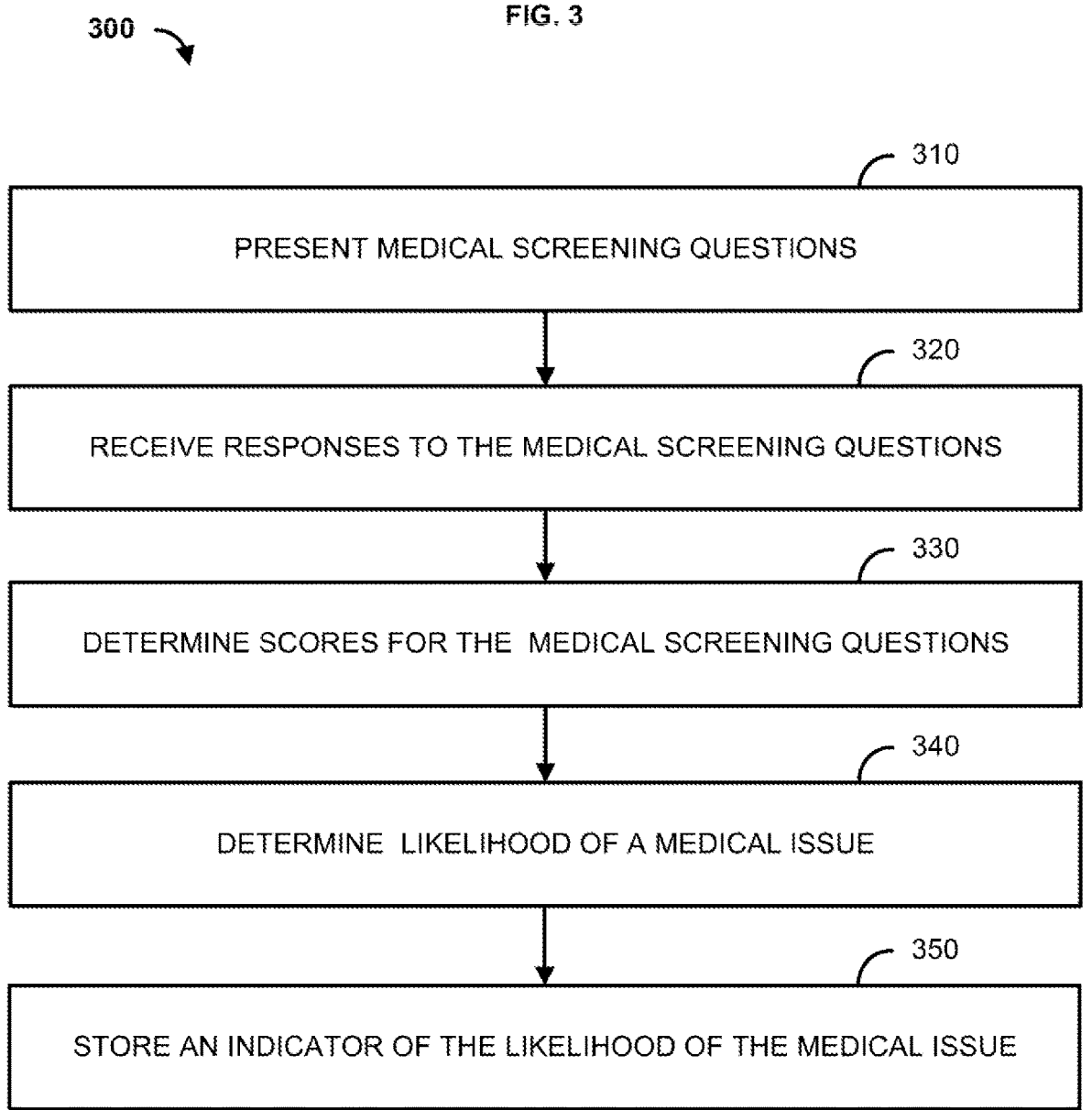
FIG. 3 shows a flowchart of an example method for comprehensive patient screening.

FIG. 3 shows a flowchart of an example method 300 for comprehensive patient screening. To aid in the provision of health care to users (e.g., veterans, medical screening patients, health care participants, etc.), at 310, a user device (e.g., a mobile device, a smart device, computing device, etc.) may present, display, and/or cause display of a plurality of medical screening questions. For example, the user device may include and/or be associated with a display for presenting/displaying a plurality of medical screening questions. In some instances, the user device may be configured with an application that causes a plurality of medical screening questions to be presented and/or displayed. The plurality of medical screening questions may include questions associated with a plurality of measures associated with health and wellbeing.

The plurality of measures may include measures and/or information associated with a user's sociodemographic and service history, military sexual trauma (MST), traumatic brain injury (TBI), somatic symptoms (e.g., pain in various areas, dizziness, cardiovascular issues/concerns, gastrointestinal issues/concerns, and fatigue/sleep issues/concerns, etc.), pain intensity, tobacco and alcohol use, posttraumatic stress disorder (PTSD) symptoms, depression symptoms, anxiety symptoms, insomnia, and/or the like. The plurality of measures may include measures and/or information associated with any health and/or wellbeing issue.

Questions and/or measures for sociodemographic and service history may include and/or be used to determine a user's age, gender, race, ethnicity, education level, relationship status, primary sources of income, and/or the like. For example, a user such as a military/war veteran, via the user device, may be presented questions that elicit responses and/or information associated with pay grade, a branch of service, number of deployments, and exposure to combat. Questions and/or measures for sociodemographic and service history may be associated with any question and/or query that elicits a response from the user. Questions and/or measures for sociodemographic and service history may be any questions and/or measures for sociodemographic and service history.

Questions and/or measures for military sexual trauma (MST) may include and/or be associated with sexual activity while in active duty. For example, a measure for MST may be associated with a question such as "when you were in the military, did you ever receive uninvited and unwanted sexual attention (e.g., unwanted touching, cornering, pressure for sexual favors, verbal remarks, etc.)?," and "when you were in the military, did anyone ever use force or the threat of force to have sex with you against your will?" Questions and/or measures for MST may be associated with any question and/or query that elicits a response from the user. Questions and/or measures for MST may be any questions and/or measures for MST.

Questions and/or measures for traumatic brain injury (TBI) may include and/or be associated with events occurring during a user's military tenure in which an injury could have occurred, immediate symptoms following the event, as well as current, new, and/or worsening symptoms. Questions and/or measures for TBI may be associated with any question and/or query that elicits a response from the user. Questions and/or measures for TBI may be any questions and/or measures for TBI.

Questions and/or measures for somatic symptoms may be used to assess and/or determine a user's somatic symptoms. For example, user's may be queried regarding the extent that the user is bothered by pain in various areas, dizziness, cardiovascular problems, gastrointestinal issues, and fatigue or sleep problems. Questions and/or measures for somatic symptoms may be associated with any question and/or query that elicits a response from the user. Questions and/or measures for somatic symptoms may be any questions and/or measures for somatic symptoms and/or the like.

Questions and/or measures for pain intensity, posttraumatic stress disorder (PTSD), depression symptoms, anxiety symptoms, and insomnia may include and/or be associated with any question and/or query that elicits a response from the user. Questions and/or measures for pain intensity, PTSD, depression symptoms, anxiety symptoms, and insomnia may be any questions and/or measures for and/or associated with pain intensity, posttraumatic stress disorder (PTSD), depression symptoms, anxiety symptoms, insomnia, and/or the like.

The user device may present, display, and/or cause display of any question, inquiry, and/or the like associated with user health and wellbeing. The user device may present, display, and/or cause display of any question, inquiry, and/or the like.

At 320, responses to the plurality of medical screening questions may be received. The user device may receive responses to the medical screening questions. The responses to the medical screening questions may include tactile responses, audio responses, and/or any other response associated with a user. For example, the user device may present, display, and/or cause display of a question relating to MST such as "when you were in the military, did you ever receive uninvited and unwanted sexual attention (e.g., unwanted touching, cornering, pressure for sexual favors, verbal remarks, etc.)?" The user may provide a response, such as "yes," or "no" to the question by providing an audible response, clicking on and/or accessing a displayed field, typing a response via an input/output component of the user device (e.g., keyboard, touch screen, etc.), and/or any other means of providing a response.

At 330, one or more scores may be determined. A score (e.g., a dichotomous score, a polytomous score, etc.) may be determined for each measure of the plurality of measures, based on the response to each of the plurality of medical screening questions. Each measure of the plurality of measures may be associated with a scale (e.g., a nominal scale, an ordinal scale, an interval scale, a ratio scale, etc.) of a plurality of scales. Each scale of the plurality of scales may a quantitative and/or a standard system for grading a measure of the plurality of measures. The one or more scores may be determined by determining, for each measure of the plurality of measures, a scale of the plurality of scales. Each response to the plurality of medical screening questions, based on an associated scale of the plurality of scales, may be scaled. Each scaled response to the plurality of medical screening questions may represent a score of the one or more scores. In some instances, each score of the one or more scores may be totaled (e.g., summed, averaged, means-squared, etc.) to determine an overall score associated with the user. The overall score may be associated with the health and/or wellbeing of the user. The overall score may indicate possible health and/or wellbeing issues.

In some instances, the user device may determine the one or more scores. For instance, an application associated with and/or installed on the user device may determine the one or more scores based on the responses to the plurality of medical screening questions. The user device may determine the one or more scores based on any method. In some instances, a computing device (e.g., cloud-based device, server, electronic medical records management device, etc.) may determine the one or more scores. For example, the user device may receive the responses to the plurality of medical screening questions and send the responses to the computing device. The user device may send the responses to the computing device via a long-range communication technique (e.g., Internet, cellular, satellite, and the like), via a short-range communication technique (e.g., BLUETOOTH®, ZigBee, Z-wave, near-field communication, infrared, etc.), and/or via any communication technique. The computing device may receive the responses to the plurality of medical screening questions and determine the one or more scores. The computing device may access data/information associated with the plurality of measures to determine the one or more scores. The computing device may determine the one or more scores by any method and may provide the one or more scores to the user device. The computing device may provide the one or more scores to the user device via a long-range communication technique (e.g., Internet, cellular, satellite, and the like), via a short-range communication technique (e.g., BLUETOOTH®, ZigBee, Z-wave, near-field communication, infrared, etc.), and/or via any communication technique.

The one or more scores may be stored. Storing the one or more scores may include associating the one or more scores with user information (e.g., a user profile, an electronic medical record (EMR) associated with the patient, a user account, etc.) associated with the user. Storing the one or more scores may include storing at least the score for each measure of the plurality of measures. Storing the one or more scores may include storing additional data/information associated with the user.

In some instances, the user device may store the one or more scores. For example, an application associated with the user device may access and/or be in communication with a data/information repository (e.g., an electronic medical record, etc.) associated with the user device. In some instances, the computing device may store the one or more scores. The computing device may include and/or be associated with an electronic medical record (EMR). For example, the user device may establish a communication session with the computing device. The user device may send the computing device a device identifier associated with the user device and an identifier associated with the user, such as a patient identifier and/or the like. The computing device may use the device identifier to authenticate the user device. For example, the computing device may associate the device identifier with stored user information (e.g., a user profile, an electronic medical record (EMR) associated with the patient, a user account, a whitelist, etc.). The user information may indicate one or more devices (e.g., user devices) that are authenticated and/or authorized to access an EMR system. The computing device may use the identifier associated with the user (e.g., patient identifier, etc.) to authenticate the user. For example, the computing device may associate the identifier associated with the user (e.g., patient identifier, etc.) with stored user information (e.g., a user profile, an electronic medical record (EMR) associated with the patient, a user account, a whitelist, etc.). The user information may indicate one or more users (e.g., patients, subjects, etc.) that are authenticated and/or authorized to access and/or be associated with the EMR system. The computing device may determine, based on the identifier associated with the user (e.g., patient identifier, etc.), information associated with the user, such as an electronic medical record (EMR) and/or the like.

An EMR associated with a user may include data/information such as a treatment and medical history associated with the user. The EMR may include the user's health (e.g., mental health, etc.) history and records cataloged in a standardized format. The EMR may be and/or include secure and/or encrypted data/information that may be searched, accessed, and/or queried to provide real-time information associated with medical decision-making. The one or more scores may be associated with the EMR associated with the user.

At 340, a likelihood that the user will be diagnosed with a medical issue related to a measure of the plurality of measures may be determined. For example, the one or more scores may be compiled with additional medical information associated with each measure of the plurality of measures, and specific diagnosis, and prescribed services and/or treatments may be determined based on a score for each measure of the plurality of measures. In some instances, the user device may determine the likelihood that the user will be diagnosed with a medical issue related to a measure of the plurality of measures. For example, an application associated with the user device may determine the likelihood that the user will be diagnosed with a medical issue related to a measure of the plurality of measures. In some instances, the computing device (and/or a device/system in communication with the computing device, etc.) may determine the likelihood that the user will be diagnosed with a medical issue related to a measure of the plurality of measures based on the responses received from the user device.

The likelihood that the user will be diagnosed with a medical issue related to a measure of the plurality of measures may be associated with an alert condition. An alert condition may be determined based on a score for a measure of the plurality of measures. An alert condition may be and/or include an indication that the user is at risk for an emergency medical condition associated with a measure of the plurality of measures. The one or more scores may be compiled with additional medical information associated with each measure of the plurality of measures, and specific diagnosis, and prescribed services and/or treatments may be determined based on an alert condition. In some instances, the user device may determine the alert condition. For example, an application associated with the user device may determine the alert condition. In some instances, the computing device (and/or a device/system in communication with the computing device, etc.) may determine the alert condition based on the responses received from the user device.

To determine an alert condition, each score of the one or more scores may be accessed and/or analyzed according to one or more rules associated with each measure of the plurality of measures. For example, a rule associated with a measure for pain intensity may dictate that user scores that satisfy a threshold value may indicate an alert condition. Such that a score/value of 4 or greater (on an associated scale ranging from values 1-10) are considered to be clinically significant pain, and therefore indicative of an alert condition. An alert condition may be determined based on any rule associated with each measure of the plurality of measures.

In some instances, a neural network and/or machine learning (e.g., a machine learning device/module/system, etc.) may determine an alert condition and/or the likelihood that the user will be diagnosed with a medical issue related to a measure of the plurality of measures, based on a score for the measure. The computing device and/or the user device may be in communication with (and/or comprise) the neural network (e.g., a machine learning device/module/system, etc.). The neural network may include contemporaneous determined and stored user health data (e.g., from medical screening questions, etc.). The neural network may comprise a collection of clinical data/information, such as historical symptoms, diagnoses, and outcomes, along with time development of medical issues and measures associated with a sociodemographic and service history, military sexual trauma (MST), traumatic brain injury (TBI), somatic symptoms (e.g., pain in various areas, dizziness, cardiovascular issues/concerns, gastrointestinal issues/concerns, and fatigue/sleep issues/concerns, etc.), pain intensity, tobacco and alcohol use, posttraumatic stress disorder (PTSD) symptoms, depression symptoms, anxiety symptoms, insomnia, and/or the like. The clinical data/information may be coded and/or encoded and input into the neural network to populate and/or train the network with clinical data/information that may be used to determine, derived, and/or predict clinical, medical, health, and diagnostic outcomes, such as one or more alerts conditions.

Scores derived from responses to the medical screening questions may be used to create a dataset. The dataset may be compared to datasets and/or information stored by the neural network. Comparing the dataset to datasets and/or information stored by the neural network may provide an indication of a possible diagnosis of a medical issue associated with a measure of the plurality of measures. In some instances, scores derived from responses to the medical screening questions from multiple users and/or user devices may be used to create a training dataset. The training dataset may be used to train the neural network. When new data/information (e.g., clinical information, responses to medical screening questions, training datasets, etc.) is provided to the neural network, the network may update any stored data/information and adapt to any changing parameters (e.g., changes to a dataset, etc.) associated with the clinical data/information. The neural network (and/or a use of the neural network) may verify conclusions, diagnoses, and/or the like for accuracy and/or significance. The neural network may store test cases, appropriate outcomes and the relative occurrence of misidentification of the proper outcome and/or diagnosis. The neural network may establish a threshold of acceptable misidentifications or misdiagnoses.

When an alert condition (and/or any other condition associated with the plurality of medical screening questions) is determined, such as based on a score for a measure of the plurality of measures, a clinical device (e.g., the clinical device 107, a server, etc.) and/or an associated clinician may be determined. In some cases, the user device, based on determining the alert condition, may determine the clinical device and/or an associated clinician. For example, an application associated with and/or installed on the user device, based on determining the alert condition, may determine the clinical device and/or an associated clinician. In some cases, the computing device, based on determining the alert condition, may determine the clinical device and/or an associated clinician.

In some instances, the device identifier associated with the user device and/or the identifier associated with the user may be used to determine the clinical device and/or an associated clinician. For example, the device identifier associated with the user device and/or the identifier associated with the user may be used to determine the user information (e.g., user profile, electronic medical record (EMR) associated with the patient, user account, whitelist, etc.). The user information may indicate one or more clinical devices and/or clinicians associated with the user and/or user device. The one or more clinical devices and/or clinicians may each be associated with a measure (or one or more measures) of the plurality of measures. In some instances, the one or more clinical devices and/or clinicians may be determined based on a measure of the plurality of measures, such as based on a score derived from the plurality of medical questions for a particular measure of the plurality of measures. For example, each measure of the plurality of measures may be associated with one or more clinical devices and/or clinicians. The one or more one or more clinical devices and/or clinicians may be associated with a respective measure of the plurality of measures based on a clinical ability of a clinician associated with a clinical device to respond to, treat, diagnose, provide care for, and/or otherwise address any issue relating to and/or associated with the measure. The one or more clinical devices and/or clinicians may each be ranked based on a clinical ability of a clinician associated with a clinical device to respond to, treat, diagnose, provide care for, and/or otherwise address any issue relating to and/or associated with the measure. The rank associated with the clinical device and/or an associated clinician may be used to determine the clinical device and/or an associated clinician.

The clinical device (e.g., the clinical device 107, a server, etc.) and/or an associated clinician may receive a notification (e.g., a signal, a message, an email, a text, etc.). In some cases, the user device, based on determining the alert condition, may send the notification to the clinical device. For example, an application associated with and/or installed on the user device, based on determining the alert condition, may send the notification to the clinical device. In some cases, the computing device, based on determining the alert condition, may send the notification to the clinical device. The notification may be sent to the clinical device via a long-range communication technique (e.g., Internet, cellular, satellite, and the like), via a short-range communication technique (e.g., BLUETOOTH®, ZigBee, Z-wave, near-field communication, infrared, etc.), and/or via any communication technique. The notification may be sent to the clinical device via an application associated with and/or installed on the user device, associated with the computing device, and/or the like. For example, the notification may be sent to the clinical device via an application program interface (API) associated with the user device, the computing device, the clinical device, and/or the like.

The notification may cause the clinical device to perform an action. For example, the notification may cause the clinical device to schedule an appointment (e.g., via an appointment scheduling system, online/web-based system, etc.) to meet with the clinician and/or a clinical staff associated with the clinical device. The notification may cause the clinical device to send data/information associated with the user of the user device to the user device and/or computing device. The data/information associated with the user of the user device may include appointment reminders, health and/or medical advice/instructions, information relating to a measure of the plurality of measures, and/or the like. The data/information associated with the user may include any data/information.

At 350, an indicator of the likelihood that the user will be diagnosed with a medical issue associated with a measure of the plurality of measures may be stored. Storing the indicator of the likelihood that the user will be diagnosed with a medical issue associated with a measure of the plurality of measures may include associating the indicator with the user information (e.g., user profile, the electronic medical record (EMR) associated with the patient, user account, etc.) associated with the user. In some instances, the user device may store the indicator of the likelihood that the user will be diagnosed with a medical issue associated with a measure of the plurality of measures. For example, an application associated with the user device may access and/or be in communication with the data/information repository (e.g., electronic medical record, etc.) associated with the user device. In some instances, the computing device may store the indicator of the likelihood that the user will be diagnosed with a medical issue associated with a measure of the plurality of measures. The computing device may include and/or be associated with the electronic medical record (EMR) associated with the user. For example, the user device may establish a communication session with the computing device. The user device may send the computing device the device identifier associated with the user device and the identifier associated with the user (e.g., patient identifier, etc.). The computing device may use the device identifier to authenticate the user device. For example, the computing device may associate the device identifier with stored user information (e.g., a user profile, an electronic medical record (EMR) associated with the patient, a user account, a whitelist, etc.). The user information may indicate one or more devices (e.g., user devices) that are authenticated and/or authorized to access the EMR system. The computing device may use the identifier associated with the user (e.g., patient identifier, etc.) to authenticate the user. For example, the computing device may associate the identifier associated with the user (e.g., patient identifier, etc.) with stored user information (e.g., a user profile, an electronic medical record (EMR) associated with the patient, a user account, a whitelist, etc.). The user information may indicate one or more users (e.g., patients, subjects, etc.) that are authenticated and/or authorized to access and/or be associated with the EMR system. The computing device may determine, based on the identifier associated with the user (e.g., patient identifier, etc.), the EMR associated with the user. The indicator of the likelihood that the user will be diagnosed with a medical issue associated with a measure of the plurality of measures may be stored with the EMR associated with the user.

FIG. 4 shows a flowchart of an example method 400 for comprehensive patient screening. To aid in the provision of health care to users (e.g., veterans, medical screening patients, health care participants, etc.), a plurality of medical screening questions may be generated and/or determined. At 410, a computing device (e.g., cloud-based device, server, electronic medical records management device, etc.) may generate and/or determine the plurality of medical screening questions. The plurality of medical screening questions may include questions associated with a plurality of measures associated with health and wellbeing.

The plurality of measures may include measures and/or information associated with a user's sociodemographic and service history, military sexual trauma (MST), traumatic brain injury (TBI), somatic symptoms (e.g., pain in various areas, dizziness, cardiovascular issues/concerns, gastrointestinal issues/concerns, and fatigue/sleep issues/concerns, etc.), pain intensity, tobacco and alcohol use, posttraumatic stress disorder (PTSD) symptoms, depression symptoms, anxiety symptoms, insomnia, and/or the like. The plurality of measures may include measures and/or information associated with any health and/or wellbeing issue.

Questions and/or measures for sociodemographic and service history may include and/or be used to determine a user's age, gender, race, ethnicity, education level, relationship status, primary sources of income, and/or the like. For example, a user such as a military/war veteran, via the user device, may be presented questions that elicit responses and/or information associated with pay grade, a branch of service, number of deployments, and exposure to combat. Questions and/or measures for sociodemographic and service history may be associated with any question and/or query that elicits a response from the user. Questions and/or measures for sociodemographic and service history may be any questions and/or measures for sociodemographic and service history.

Questions and/or measures for military sexual trauma (MST) may include and/or be associated with sexual activity while in active duty. For example, a measure for MST may be associated with a question such as "when you were in the military, did you ever receive uninvited and unwanted sexual attention (e.g., unwanted touching, cornering, pressure for sexual favors, verbal remarks, etc.)?" and "when you were in the military, did anyone ever use force or the threat of force to have sex with you against your will?" Questions and/or measures for MST may be associated with any question and/or query that elicits a response from the user. Questions and/or measures for MST may be any questions and/or measures for MST.

Questions and/or measures for traumatic brain injury (TBI) may include and/or be associated with events occurring during a user's military tenure in which an injury could have occurred, immediate symptoms following the event, as well as current, new, and/or worsening symptoms. Questions and/or measures for TBI may be associated with any question and/or query that elicits a response from the user. Questions and/or measures for TBI may be any questions and/or measures for TBI.

Questions and/or measures for somatic symptoms may be used to assess and/or determine a user's somatic symptoms. For example, user's may be queried regarding the extent that the user is bothered by pain in various areas, dizziness, cardiovascular problems, gastrointestinal issues, and fatigue or sleep problems. Questions and/or measures for somatic symptoms may be associated with any question and/or query that elicits a response from the user. Questions and/or measures for somatic symptoms may be any questions and/or measures for somatic symptoms and/or the like.

Questions and/or measures for pain intensity, posttraumatic stress disorder (PTSD), depression symptoms, anxiety symptoms, and insomnia may include and/or be associated with any question and/or query that elicits a response from the user. Questions and/or measures for pain intensity, PTSD, depression symptoms, anxiety symptoms, and insomnia may be any questions and/or measures for and/or associated with pain intensity, posttraumatic stress disorder (PTSD), depression symptoms, anxiety symptoms, insomnia, and/or the like.

At 420, a plurality of user devices (e.g., mobile devices, smart devices, computing devices, etc.) may present, display, and/or cause display of the plurality of medical screening questions. For example, each user device may include and/or be associated with a display for presenting/displaying one or more questions of the plurality of medical screening questions. In some instances, each user device may be configured with an application that causes one or more questions of the plurality of medical screening questions to be presented and/or displayed. The user device may present, display, and/or cause display of any question, inquiry, and/or the like associated with user health and wellbeing. Each user device may present, display, and/or cause display of any question, inquiry, and/or the like. For example, a respective user of each user device of the plurality of user devices may access an interface, website, application, and/or the like associated with a user device of the plurality of user devices and the respective user device may present the plurality of medical screening questions.

At 430, responses to the plurality of medical screening questions may be received. Each user device of the plurality of user devices may receive responses to the medical screening questions. The responses to the medical screening questions may include tactile responses, audio responses, and/or any other response associated with a user. For example, one or more user devices of the plurality of user devices may present, display, and/or cause display of a question relating to MST such as "when you were in the military, did you ever receive uninvited and unwanted sexual attention (e.g., unwanted touching, cornering, pressure for sexual favors, verbal remarks, etc.)?" The users of the one or more user devices may respond, such as "yes," or "no" to the question by providing an audible response, clicking on and/or accessing a displayed field, typing a response via an input/output component of the user device (e.g., keyboard, touch screen, etc.), and/or any other means of providing a response. Each user device of the plurality of user devices may send responses to the plurality of medical screening questions to the computing device. Each user device of the plurality of user devices may send responses to the plurality of medical screening questions to the computing device via a long-range communication technique (e.g., Internet, cellular, satellite, and the like), via a short-range communication technique (e.g., BLUETOOTH®, ZigBee, Z-wave, near-field communication, infrared, etc.), and/or via any communication technique.

At 440, one or more scores may be determined. The computing device may determine a score (e.g., a dichotomous score, a polytomous score, etc.) for each measure of the plurality of measures, based on the responses to the plurality of medical screening questions received from each user device of the plurality of user devices. Each measure of the plurality of measures may be associated with a scale (e.g., a nominal scale, an ordinal scale, an interval scale, a ratio scale, etc.) of a plurality of scales. Each scale of the plurality of scales may a quantitative and/or a standard system for grading a measure of the plurality of measures. One or more scores may be determined, for each user device of the plurality of user devices, by determining, for each measure of the plurality of measures, a scale of the plurality of scales. Each response to the plurality of medical screening questions, based on an associated scale of the plurality of scales, may be scaled. Each scaled response to the plurality of medical screening questions may represent a score of the one or more scores. In some instances, each score of the one or more scores may be totaled (e.g., summed, averaged, means-squared, etc.) to determine an overall score associated with a user. The overall score may be associated with the health and/or wellbeing of the user. The overall score may indicate possible health and/or wellbeing issues.

The computing device may access data/information associated with the plurality of measures to determine the one or more scores. The computing device may determine one or more scores by any method and may provide one or more scores to each user device of the plurality of user device based on the respective responses to plurality of medical screening questions. The computing device may provide the one or more scores to each user device of the plurality of user devices via a long-range communication technique (e.g., Internet, cellular, satellite, and the like), via a short-range communication technique (e.g., BLUETOOTH®, ZigBee, Z-wave, near-field communication, infrared, etc.), and/or via any communication technique. The computing device may cause each user device of the plurality of user devices to display the respective scores determined from the responses to the medical screening questions presented by the respective user device.

At 450, the one or more scores may be stored. Storing the one or more scores may include associating, for each user device of the plurality of user devices, the respective one or more scores with user information (e.g., a user profile, an electronic medical record (EMR) associated with the patient, a user account, etc.) associated with each user of each user device of the plurality of user devices. Storing the one or more scores may include storing, for each user of each user device of the plurality of user devices, at least the score for each measure of the plurality of measures. Storing the one or more scores for each user of each user device of the plurality of user devices may include storing additional data/information associated with each user of each user device of the plurality of user devices.

The computing device may include and/or be associated with an electronic medical record (EMR) system. Each user device of the plurality of user devices may send the computing device a device identifier associated with the respective user device and an identifier associated with the respective user, such as a patient identifier and/or the like. The computing device, for each user device of the plurality of user devices, may use the device identifier to authenticate the user device. For example, the computing device may associate the device identifier with stored user information (e.g., a user profile, an electronic medical record (EMR) associated with the patient, a user account, a whitelist, etc.). The user information associated with each user/user device may indicate one or more devices (e.g., user devices) that are authenticated and/or authorized to access the EMR system. The computing device, for each user device of the plurality of user devices, may use the identifier associated with the user (e.g., patient identifier, etc.) to authenticate the user. For example, the computing device may associate the identifier associated with the user (e.g., patient identifier, etc.) with stored user information (e.g., a user profile, an electronic medical record (EMR) associated with the patient, a user account, a whitelist, etc.). The user information may indicate one or more users (e.g., patients, subjects, etc.) that are authenticated and/or authorized to access and/or be associated with the EMR system. The computing device may determine, for each user device of the plurality of user devices, based on the identifier associated with the user (e.g., patient identifier, etc.), information associated with the user, such as an electronic medical record (EMR) and/or the like.

An EMR associated with a user may include data/information such as a treatment and medical history associated with the user. The EMR may include the user's health (e.g., mental health, etc.) history and records cataloged in a standardized format. The EMR may be and/or include secure and/or encrypted data/information that may be searched, accessed, and/or queried to provide real-time information associated with medical decision-making. The one or more scores may be associated with the EMR associated with the user.

At 460, one or more diagnoses, for each user of each user device of the plurality of user devices associated with the one or more scores may be determined and/or stored. A diagnosis associated with a score may be based on a likelihood that the user will experience a medical issue related to a measure of the plurality of measures. For example, for each user of each user device of the plurality of user devices, one or more scores may be compiled with additional medical information associated with each measure of the plurality of measures, and specific diagnosis, and prescribed services and/or treatments may be determined based on a score for each measure of the plurality of measures.

At 470, for each user of each user device of the plurality of user devices, data indicative of the scores and the one or more diagnoses associated with the one or more scores may be provided to a neural network and/or machine learning (e.g., a machine learning device/module/system, etc.). The neural network may include contemporaneous determined and stored user health data (e.g., from medical screening questions, etc.). The neural network may comprise a collection of clinical data/information, such as historical symptoms, diagnoses, and outcomes, along with time development of medical issues and measures associated with a sociodemographic and service history, military sexual trauma (MST), traumatic brain injury (TBI), somatic symptoms (e.g., pain in various areas, dizziness, cardiovascular issues/concerns, gastrointestinal issues/concerns, and fatigue/sleep issues/concerns, etc.), pain intensity, tobacco and alcohol use, posttraumatic stress disorder (PTSD) symptoms, depression symptoms, anxiety symptoms, insomnia, and/or the like. The clinical data/information may be coded and/or encoded and input into the neural network to populate and/or train the network with clinical data/information that may be used to determine, derived, and/or predict clinical, medical, health, and diagnostic outcomes.

Scores derived from responses to the medical screening questions may be used to create a dataset. The dataset may be compared to datasets and/or information stored by the neural network. Comparing the dataset to datasets and/or information stored by the neural network may indicate a possible diagnosis of a medical issue associated with a measure of the plurality of measures. In some instances, scores derived from responses to the medical screening questions from multiple users and/or user devices may be used to create a training dataset. The training dataset may be used to train the neural network. When new data/information (e.g., clinical information, responses to medical screening questions, training datasets, etc.) is provided to the neural network, the network may update any stored data/information and adapt to any changing parameters (e.g., changes to a dataset, etc.) associated with the clinical data/information. The neural network (and/or use of the neural network) may verify conclusions, diagnoses, and/or the like for accuracy and/or significance. The neural network may store test cases, appropriate outcomes, and the relative occurrence of misidentification of the proper outcome and/or diagnosis. The neural network may establish a threshold of acceptable misidentifications or misdiagnoses.

At 480, a determination may be made as to whether each score of the one or more scores are predictive of an associated diagnosis. The neural network may use clinical data/information, such as historical symptoms, diagnoses, and outcomes, along with time development of medical issues and measures associated with a sociodemographic and service history, military sexual trauma (MST), traumatic brain injury (TBI), somatic symptoms (e.g., pain in various areas, dizziness, cardiovascular issues/concerns, gastrointestinal issues/concerns, and fatigue/sleep issues/concerns, etc.), pain intensity, tobacco and alcohol use, posttraumatic stress disorder (PTSD) symptoms, depression symptoms, anxiety symptoms, insomnia, and/or the like in correlation with machine learning and predictive analysis to determine whether each score of the one or more scores are predictive of a diagnosis associated with a measure of the plurality of measures.

At 490, a medical screening question of the plurality of medical screening questions may be updated. The medical screening question may be updated based on scores determined for each user response to the medical screening question from each user device of the plurality of user devices. Updating the medical screening questions based on the scores determined for each user response to the medical screening question may improve the accuracy in user/patient assessment and/or diagnostic value of an associated response.

Figure 5:
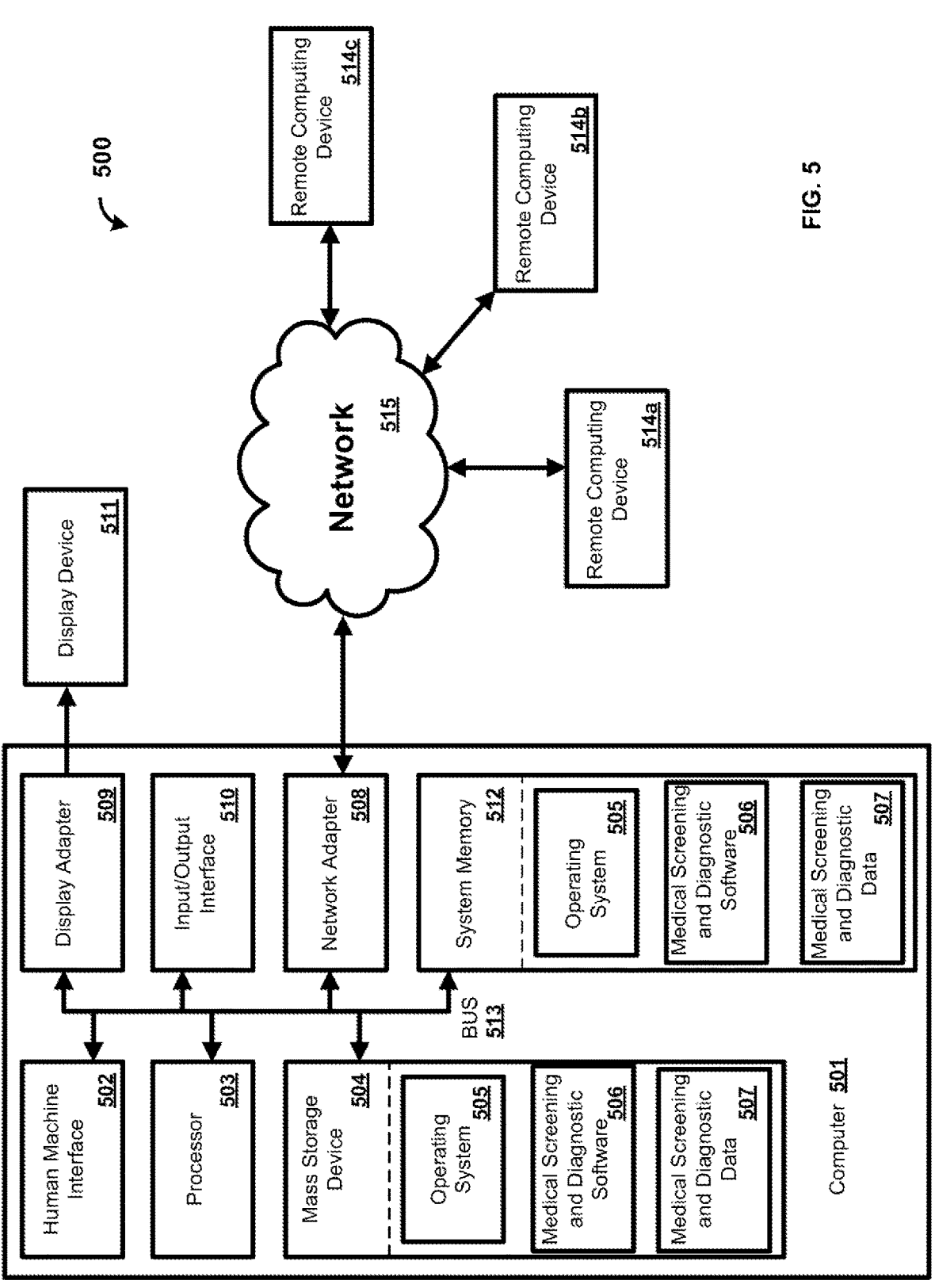
FIG. 5 shows a block diagram of an example computing device for implementing comprehensive patient screening.

FIG. 5 shows an example computing device for implementing comprehensive patient screening. Any device described herein may be a computer 501. The computer 501 may comprise one or more processors 503, a system memory 512, and a bus 513 that couples various components of the computer 501 including the one or more processors 503 to the system memory 512. In the case of multiple processors 503, the computer 501 may utilize parallel computing.

The bus 513 may comprise one or more of several possible types of bus structures, such as a memory bus, memory controller, a peripheral bus, an accelerated graphics port, and a processor or local bus using any of a variety of bus architectures.

The computer 501 may operate on and/or comprise a variety of computer-readable media (e.g., non-transitory). Computer-readable media may be any available media that is accessible by the computer 501 and comprises, non-transitory, volatile and/or non-volatile media, removable and non-removable media. The system memory 512 has computer-readable media in the form of volatile memory, such as random access memory (RAM), and/or non-volatile memory, such as read-only memory (ROM). The system memory 512 may store data such as medical screening and diagnostic data 507 and/or program modules such as operating system 505 and medical screening and diagnostic software 506 that are accessible to and/or are operated on by the one or more processors 503.

The computer 501 may also comprise other removable/non-removable, volatile/non-volatile computer storage media. The mass storage device 504 may provide non-volatile storage of computer code, computer-readable instructions, data structures, program modules, and other data for the computer 501. The mass storage device 504 may be a hard disk, a removable magnetic disk, a removable optical disk, magnetic cassettes or other magnetic storage devices, flash memory cards, CD-ROM, digital versatile disks (DVD) or other optical storage, random access memories (RAM), read-only memories (ROM), electrically erasable programmable read-only memory (EEPROM), and the like.

Any number of program modules may be stored on the mass storage device 504. An operating system 505 and medical screening and diagnostic software 506 may be stored on the mass storage device 504. One or more of the operating system 505 and medical screening and diagnostic software 506 (or some combination thereof) may comprise program modules and the medical screening and diagnostic software 506. Medical screening and diagnostic data 507 may also be stored on the mass storage device 504. Medical screening and diagnostic data 507 may be stored in any of one or more databases known in the art. The databases may be centralized or distributed across multiple locations within the network 515.

A user may enter commands and information into the computer 501 via an input device (not shown). Such input devices comprise, but are not limited to, a keyboard, pointing device (e.g., a computer mouse, remote control), a microphone, a joystick, a scanner, tactile input devices such as gloves, and other body coverings, motion sensor, and the like These and other input devices may be connected to the one or more processors 503 via a human-machine interface 502 that is coupled to the bus 513, but may be connected by other interface and bus structures, such as a parallel port, game port, an IEEE 1394 Port (also known as a Firewire port), a serial port, network adapter 508, and/or a universal serial bus (USB).

A display device 511 may also be connected to the bus 513 via an interface, such as a display adapter 509. It is contemplated that the computer 501 may have more than one display adapter 509 and the computer 501 may have more than one display device 511. A display device 511 may be a monitor, an LCD (Liquid Crystal Display), a light emitting diode (LED) display, a television, smart lens, smart glass, and/or a projector. In addition to the display device 511, other output peripheral devices may comprise components such as speakers (not shown) and a printer (not shown) which may be connected to the computer 501 via Input/Output Interface 510. Any step and/or result of the methods may be output (or caused to be output) in any form to an output device. Such output may be any form of visual representation, including, but not limited to, textual, graphical, animation, audio, tactile, and the like. The display 511 and computer 501 may be part of one device, or separate devices.

The computer 501 may operate in a networked environment using logical connections to one or more remote computing devices 514*a,b,c*. A remote computing device 514*a,b,c* may be a personal computer, computing station (e.g., workstation), portable computer (e.g., laptop, mobile phone, tablet device), smart device (e.g., smartphone, smartwatch, activity tracker, smart apparel, smart accessory), security and/or monitoring device, a server, a router, a network computer, a peer device, edge device or other common network nodes, and so on. Logical connections between the computer 501 and a remote computing device 514*a,b,c* may be made via a network 515, such as a local area network (LAN) and/or a general wide area network (WAN). Such network connections may be through a network adapter 508. A network adapter 508 may be implemented in both wired and wireless environments. Such networking environments are conventional and commonplace in dwellings, offices, enterprise-wide computer networks, intranets, and the Internet.

Application programs and other executable program components such as the operating system 505 are shown herein as discrete blocks, although it is recognized that such programs and components may reside at various times in different storage components of the computing device 501, and are executed by the one or more processors 503 of the computer 501. An implementation of medical screening and diagnostic software 506 may be stored on or sent across some form of computer-readable media. Any of the disclosed methods may be performed by processor-executable instructions embodied on computer-readable media.

While specific configurations have been described, it is not intended that the scope be limited to the particular configurations set forth, as the configurations herein are intended in all respects to be possible configurations rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible nonexpress basis for interpretation, including: matters of logic with respect to arrangement of steps or operational flow; plain meaning derived from grammatical organization or punctuation; the number or type of configurations described in the specification.

It will be apparent to those skilled in the art that various modifications and variations may be made without departing from the scope or spirit. Other configurations will be apparent to those skilled in the art from consideration of the specification and practice described herein. It is intended that the specification and described configurations be considered as exemplary only, with a true scope and spirit being indicated by the following claims.

What is claimed is:

1. A method comprising:

receiving, via a user device, a plurality of responses to a plurality of screening questions from a user, wherein each screening question is associated with a symptomatic indicator of a plurality of symptomatic indicators;

determining, by the user device for each symptomatic indicator of the plurality of symptomatic indicators, based on the response to each of the plurality of screening questions, a score;

receiving, at the user device from an interface associated with the user device, one or more physiological or behavioral signals captured by one or more sensors, wherein the physiological or behavioral signals comprise at least one of audio sensor data, video sensor data, or motion sensor data;

determining, by the user device based on the score for each symptomatic indicator of the plurality of symptomatic indicators and the one or more physiological or behavioral signals, a profile comprising the aggregated user health data;

sending the profile comprising aggregated user health data to a computing device;

receiving, from the computing device based on the profile, an alert condition including an indication that the user is at risk of an emergency medical condition, wherein the computing device comprises a machine learning model comprising a neural network trained on profiles and corresponding prior diagnoses and is configured to determine the alert condition; and sending, from the user device to a clinical device, the alert condition.

2. The method of claim 1, wherein storing the profile comprises:

establishing a communication session between the user device and a computing device system;

receiving, by the computing device, a device identifier of the user device and a user identifier of the user;

authenticating, based on a device identifier, the user device;

authenticating, based on the user identifier, the user; and storing, based on authenticating the user device and the user, the profile.

3. The method of claim 1, further comprising encrypting at least one of, the device identifiers, the user identifier, or the score for each response of the plurality of responses.

4. The method of claim 1, wherein the alert condition for the user is further determined based on at least one score for a symptomatic indicator of the plurality of symptomatic indicators.

5. The method of claim 4, wherein the alert condition is determined based on the score satisfying a threshold.

6. The method of claim 5, further comprising:

determining a clinician associated with a type of the alert condition; and determining, based on the clinician, the clinical device.

7. The method of claim 1, wherein the user device comprises one or more of, a mobile phone, a tablet computer, a laptop computer, or a desktop computer.

8. The method of claim 1, wherein the interface comprises one or more of an accelerometer, a pedometer, a geographical position sensing (GPC) module, an oximeter, or a tactile sensor.

9. The method of claim 1, further comprising sending, based on a score of the plurality of scores satisfying a threshold, a notification.

10. The method of claim 1, further comprising sending, based on a signal of the one or more signals satisfying a threshold, a notification.

11. The method of claim 1, wherein presenting, via the user device, the plurality of screening questions comprises presenting the plurality of screening questions via an application running on the user device.

12. The method of claim 1, wherein the plurality of screening questions are associated with two or more of occupational and regional exposure, military service history, somatic symptoms, physical injury, illness, pain, post-traumatic stress disorder (PTSD) symptoms, behavior, depression symptoms, and social interactions.

13. The method of claim 1, wherein determining, for each symptomatic indicator of the plurality of symptomatic indicators, based on the response to each of the plurality of screening questions, the score comprises:

determining, based on the symptomatic indicator, a scale; and scaling, based on the scale, the response to each of the plurality of screening questions, wherein the scaled response represents the score.

14. The method of claim 1, further comprising:

determining, for each of a plurality of user, a dataset comprising a score for each symptomatic indicator of the plurality of symptomatic indicators and one of, an indication of a possible diagnosis of a medical issue related to the symptomatic indicator or an indication of no likely diagnosis of a medical issue related to the symptomatic indicator;

determining, based on the dataset, a training dataset; and training, based on the training dataset, a machine learning module to determine a likelihood that another user will have a diagnosis of an issue related to the symptomatic indicator based on the score for the symptomatic indicator.

15. A method comprising:

receiving, via a user device, a plurality of responses to a plurality of screening questions from a user;

determining, for each response of the plurality of responses, a score;

receiving, from an interface associated with the user device, one or more physiological or behavioral signals captured by one or more sensors, wherein the physiological or behavioral signals comprise at least one of audio sensor data, video sensor data, or motion sensor data;

determining, based on the score for each response of the plurality of responses and the one or more physiological or behavioral signals, a profile comprising aggregated user health data;

sending the profile comprising the aggregated user health data to a computing device;

receiving, from the computing device based on the profile, an alert condition including an indication that the user is at risk of an emergency medical condition, wherein the computing device comprises a machine learning model comprising a neural network trained on profiles and corresponding prior diagnoses and is configured to determine the alert condition comparing the profile to a plurality of profiles and determining, based on comparing the profile to a plurality of profiles, wherein each profile of the plurality of profiles is associated with a respective user of a plurality of users, wherein each target area is associated with a symptomatic indicator, wherein the symptomatic indicator is associated with the alert condition; and sending, from the user device to a clinical device, the alert condition.

16. The method of claim 15 further comprising, causing display of the target area.

17. The method of claim 15, wherein the user device comprises one or more of, a mobile phone, a tablet computer, a laptop computer, or a desktop computer.

18. The method of claim 15, wherein the interface comprises one or more of an accelerometer, a pedometer, a geographical position sensing (GPC) module, an oximeter, or a tactile sensor.

19. An apparatus comprising:

one or more processors; and memory storing processor-executable instructions that, when executed by the one or more processors, cause the apparatus to:

receive a plurality of responses to a plurality of screening questions from a user;

determine, for each response of the plurality of responses, a score;

receive, from an interface associated with the user device, one or more physiological or behavioral signals captured by one or more sensors, wherein the physiological or behavioral signals comprise at least one of audio sensor data, video sensor data, or motion sensor data;

determine, based on the score for each response of the plurality of responses and the one or more physiological or behavioral signals, a profile comprising aggregated user health data;

send the profile comprising the aggregated user health data to a computing device;

receive, from the computing device based on the profile, an alert condition including an indication that the user is at risk of an emergency medical condition, wherein the computing device comprises a machine learning model comprising a neural network trained on profiles and corresponding prior diagnoses and is configured to determine the alert by comparing the profile to a plurality of profiles and determining, based on comparing the profile to a plurality of profiles, a target area, wherein each profile of the plurality of profiles is associated with a respective user of a plurality of users, wherein each target area is associated with a symptomatic indicator; and send, to a clinical device, the alert condition.

* * * * *